(12) United States Patent
Rekstad et al.

(10) Patent No.: US 10,695,067 B2
(45) Date of Patent: Jun. 30, 2020

(54) SURGICAL STAPLER, ANVIL FOR A SURGICAL STAPLER, AND A METHOD OF STAPLING TISSUE

(71) Applicant: Norwegian University of Science and Technology (NTNU), Trondheim (NO)

(72) Inventors: Lars Cato Rekstad, Trondheim (NO); Brynjulf Ystgaard, Trondheim (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 0 days.

(21) Appl. No.: 15/551,385

(22) PCT Filed: Jun. 28, 2017

(86) PCT No.: PCT/EP2017/065990
§ 371 (c)(1),
(2) Date: Jul. 9, 2018

(87) PCT Pub. No.: WO2018/002134
PCT Pub. Date: Jan. 4, 2018

(65) Prior Publication Data
US 2018/0235635 A1    Aug. 23, 2018

(30) Foreign Application Priority Data

Jun. 29, 2016  (GB) .................................. 1611306.0

(51) Int. Cl.
*A61B 17/115* (2006.01)
*A61B 17/072* (2006.01)

(52) U.S. Cl.
CPC ........ *A61B 17/1155* (2013.01); *A61B 17/072* (2013.01); *A61B 2017/07257* (2013.01); *A61B 2017/1157* (2013.01)

(58) Field of Classification Search
CPC .......................... A61B 17/1155; A61B 17/072
(Continued)

(56) References Cited

U.S. PATENT DOCUMENTS

| 5,205,459 A | 4/1993 | Brinkerhoff et al. |
| 5,271,543 A | 12/1993 | Grant et al. |

(Continued)

FOREIGN PATENT DOCUMENTS

| CN | 203 789 974 U | 8/2014 |
| CN | 105 125 248 A | 12/2015 |

(Continued)

OTHER PUBLICATIONS

International Search Report and Written Opinion, PCT/EP2017/065990, dated May 8, 2018 (18 pp.).

*Primary Examiner* — Nathaniel C Chukwurah
(74) *Attorney, Agent, or Firm* — Eversheds Sutherland (US) LLP

(57) ABSTRACT

A surgical stapler includes a proximal end and a distal end and an anvil at the distal end for providing resistance to staples during the stapling operation of the surgical stapler. The anvil may include a number of segments arranged end-to-end. The anvil is elongated in the collapsed state, the anvil being elongated generally in a first direction D1. The anvil is configured such that the segments rotate about a rotation axis along a perpendicular second direction D2 when the anvil is actuated between the deployed and the collapsed states. The anvil is configured such that adjacent segments pivot relative to each other about a pivot axis along a third direction D3 when the anvil is actuated between the deployed and collapsed states. The stapler also includes an actuator mechanism, wherein the actuator mechanism is configured to be controlled from a location on the surgical stapler towards the proximal end.

21 Claims, 18 Drawing Sheets

(58) Field of Classification Search
USPC .......................................... 227/175.1–180.1
See application file for complete search history.

(56) References Cited

U.S. PATENT DOCUMENTS

| | | | |
|---|---|---|---|
| 6,053,390 A | 4/2000 | Green et al. | |
| 6,957,758 B2 | 10/2005 | Aranyi | |
| 7,325,713 B2 | 2/2008 | Aranyi | |
| 7,364,060 B2 | 4/2008 | Milliman | |
| 7,494,038 B2 | 2/2009 | Milliman | |
| 7,516,877 B2 | 4/2009 | Aranyi | |
| 7,546,940 B2 | 6/2009 | Milliman et al. | |
| 7,857,187 B2 | 12/2010 | Milliman | |
| 8,109,426 B2 | 2/2012 | Milliman et al. | |
| 8,328,063 B2 | 12/2012 | Milliman et al. | |
| 8,353,439 B2 | 1/2013 | Baxter, III et al. | |
| 8,496,157 B2 | 7/2013 | Olson | |
| 8,540,132 B2 | 9/2013 | Marczyk et al. | |
| 8,616,428 B2 | 12/2013 | Milliman et al. | |
| 8,672,207 B2 | 3/2014 | Shelton, IV et al. | |
| 8,708,212 B2 | 4/2014 | Williams | |
| 8,783,543 B2 | 7/2014 | Shelton, IV et al. | |
| 8,801,734 B2 | 8/2014 | Shelton, IV et al. | |
| 8,801,735 B2 | 8/2014 | Shelton, IV et al. | |
| 8,827,903 B2 | 9/2014 | Shelton, IV et al. | |
| 8,893,948 B2 | 11/2014 | Williams | |
| 8,978,955 B2 | 3/2015 | Aronhalt et al. | |
| 9,010,605 B2 | 4/2015 | Olson et al. | |
| 9,016,547 B2 | 4/2015 | Mozdzierz et al. | |
| 9,033,204 B2 | 5/2015 | Shelton, IV et al. | |
| 9,113,883 B2 | 8/2015 | Aronhalt et al. | |
| 9,113,886 B2 | 8/2015 | Williams | |
| 9,125,654 B2 | 9/2015 | Aronhalt et al. | |
| 9,301,763 B2 | 4/2016 | Qiao et al. | |
| 9,345,482 B2 | 5/2016 | Olson et al. | |
| 9,451,956 B2 | 9/2016 | Balbierz et al. | |
| 9,451,962 B2 | 9/2016 | Olson | |
| 9,498,222 B2 | 11/2016 | Scheib et al. | |
| 9,517,070 B2 | 12/2016 | Mulreed | |
| 9,532,780 B2 | 1/2017 | Williams | |
| 9,532,781 B2 | 1/2017 | Milliman et al. | |
| 9,554,802 B2 | 1/2017 | Williams et al. | |
| 2001/0044656 A1 | 11/2001 | Williamson, IV et al. | |
| 2005/0205639 A1 | 9/2005 | Milliman | |
| 2006/0201989 A1* | 9/2006 | Ojeda | A61B 17/11 227/175.1 |
| 2007/0175963 A1 | 8/2007 | Bilotti et al. | |
| 2008/0058865 A1 | 3/2008 | Wilk | |
| 2011/0278346 A1 | 11/2011 | Hull et al. | |
| 2011/0282446 A1 | 11/2011 | Schulte et al. | |
| 2012/0024934 A1 | 2/2012 | Shelton, IV et al. | |
| 2012/0024935 A1 | 2/2012 | Shelton, IV et al. | |
| 2012/0029544 A1 | 2/2012 | Shelton, IV et al. | |
| 2012/0234890 A1* | 9/2012 | Aronhalt | A61B 17/07207 227/175.1 |
| 2013/0284792 A1 | 10/2013 | Ma | |
| 2014/0008413 A1 | 1/2014 | Williams | |
| 2014/0131420 A1* | 5/2014 | Nelson | A61B 17/1114 227/176.1 |
| 2014/0144968 A1 | 5/2014 | Shelton, IV | |
| 2014/0144969 A1 | 5/2014 | Scheib et al. | |
| 2014/0151429 A1 | 6/2014 | Scheib et al. | |
| 2014/0158747 A1 | 6/2014 | Measamer et al. | |
| 2014/0166728 A1 | 6/2014 | Swayze et al. | |
| 2014/0284370 A1 | 9/2014 | Sahin | |
| 2014/0291377 A1 | 10/2014 | Sahin | |
| 2014/0305987 A1 | 10/2014 | Parihar et al. | |
| 2014/0367444 A1 | 12/2014 | Williams | |
| 2015/0069108 A1 | 3/2015 | Williams | |
| 2015/0115014 A1 | 4/2015 | Matonick et al. | |
| 2015/0122869 A1 | 5/2015 | Aronhalt et al. | |
| 2015/0297237 A1 | 10/2015 | Hafner et al. | |
| 2015/0305742 A1 | 10/2015 | Williams | |
| 2015/0327853 A1 | 11/2015 | Aronhalt et al. | |
| 2015/0359532 A1 | 12/2015 | Williams | |
| 2015/0366562 A1 | 12/2015 | Williams | |
| 2016/0074033 A1 | 3/2016 | Bilotti | |
| 2016/0157855 A1 | 6/2016 | Williams | |
| 2016/0324525 A1 | 11/2016 | Scheib et al. | |
| 2016/0374665 A1 | 12/2016 | DiNardo et al. | |
| 2016/0374669 A1 | 12/2016 | Overmyer et al. | |
| 2017/0000475 A1 | 1/2017 | Sgroi, Jr. et al. | |
| 2017/0000486 A1 | 1/2017 | Penna et al. | |
| 2017/0007256 A1 | 1/2017 | Olson | |
| 2017/0042544 A1 | 2/2017 | Scheib et al. | |
| 2017/0055994 A1 | 3/2017 | Vendely et al. | |
| 2017/0079659 A1 | 3/2017 | Mulreed | |
| 2017/0086825 A1 | 3/2017 | Henderson et al. | |

FOREIGN PATENT DOCUMENTS

| | | |
|---|---|---|
| EP | 1857058 A1 | 11/2007 |
| JP | 2004 147969 A | 5/2004 |
| WO | 03/030745 A1 | 4/2003 |
| WO | 2008/040580 A1 | 4/2008 |
| WO | 2012/125615 A2 | 9/2012 |
| WO | 2014/008289 A2 | 1/2014 |
| WO | 2014/149011 A1 | 9/2014 |

\* cited by examiner

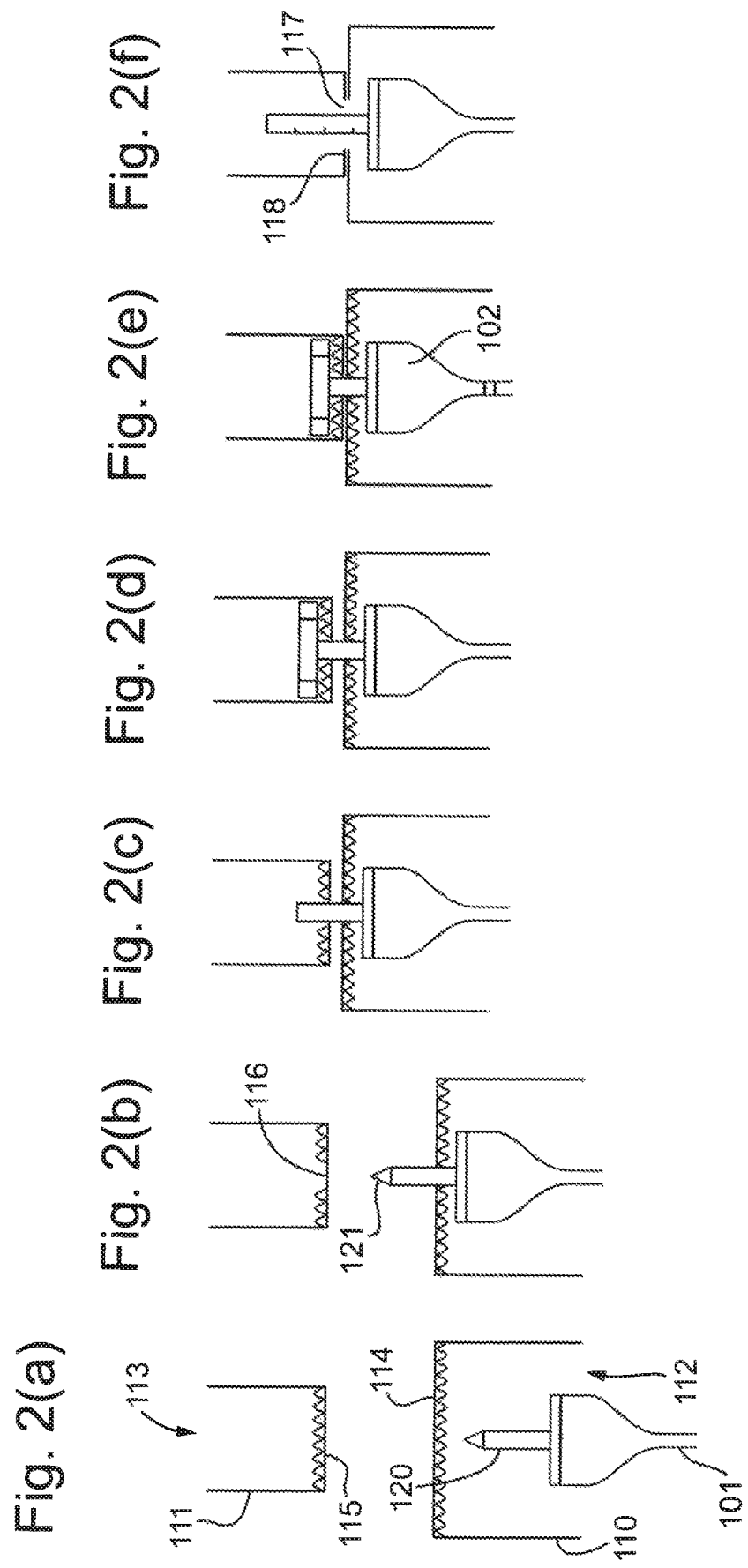

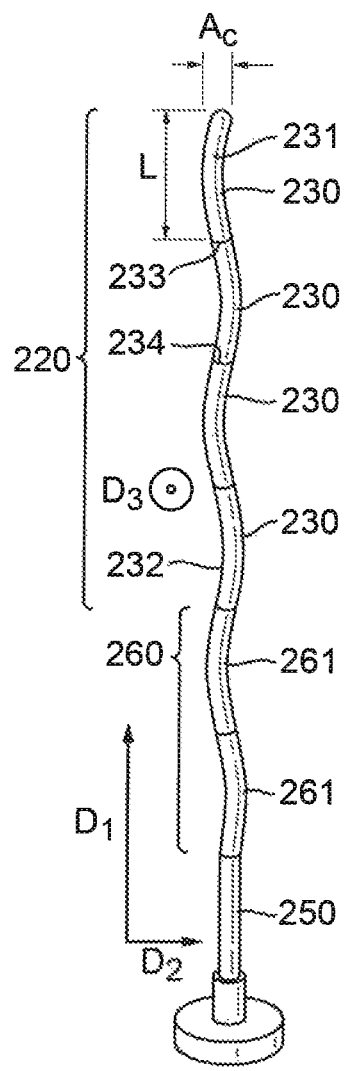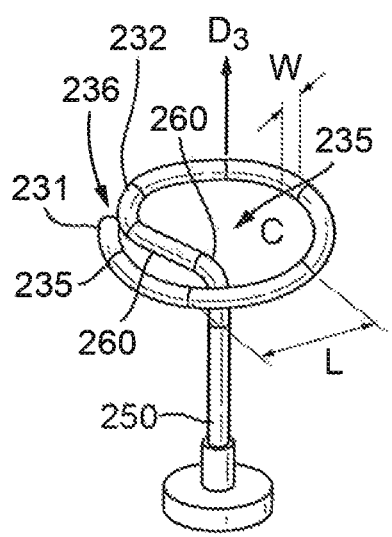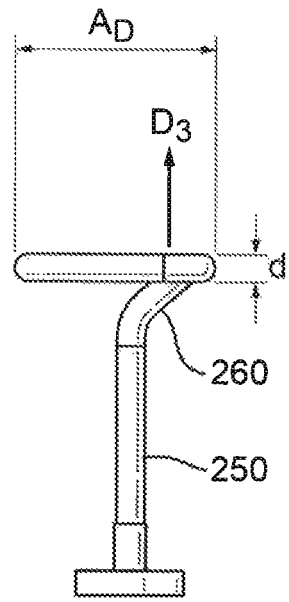

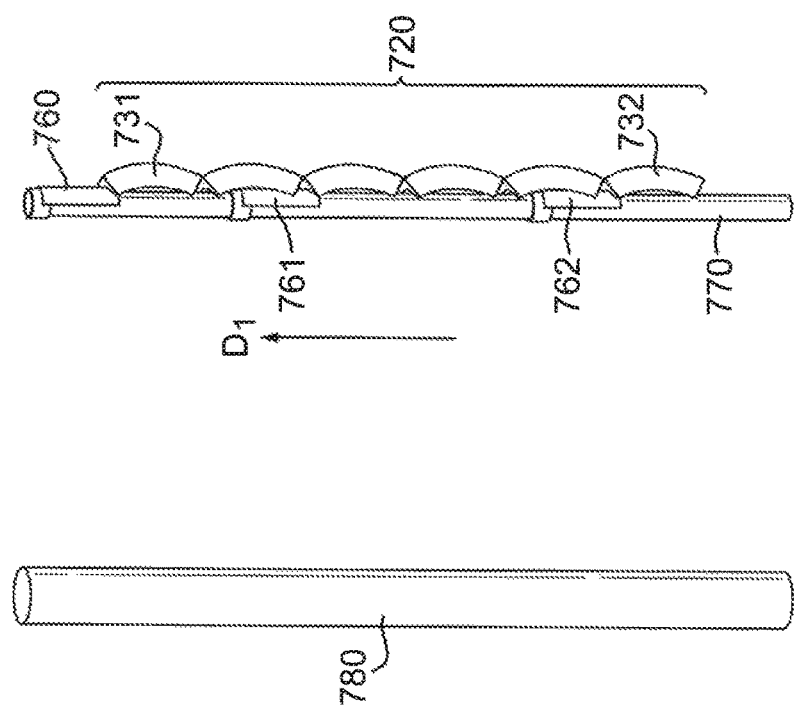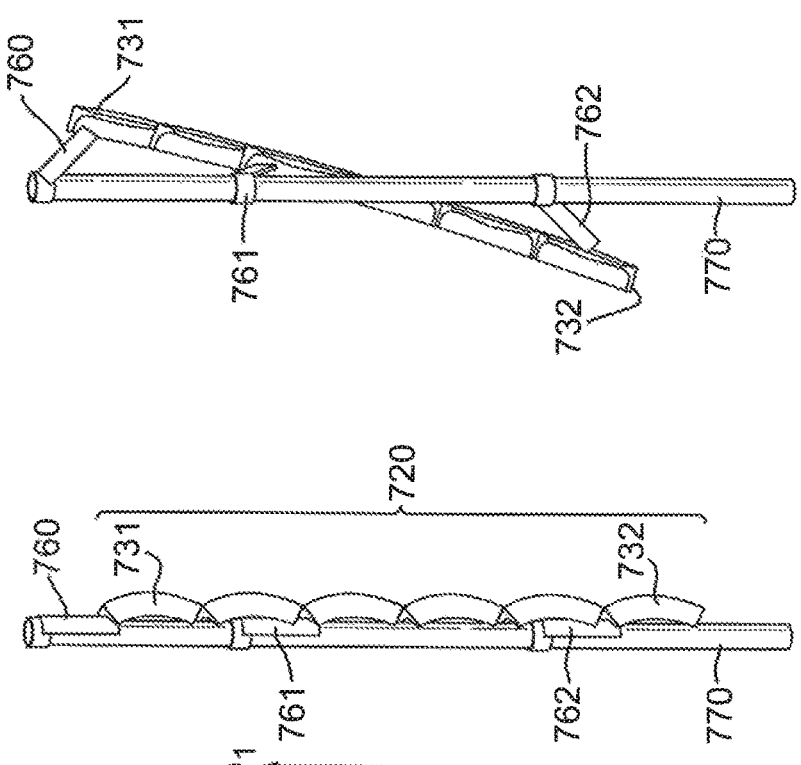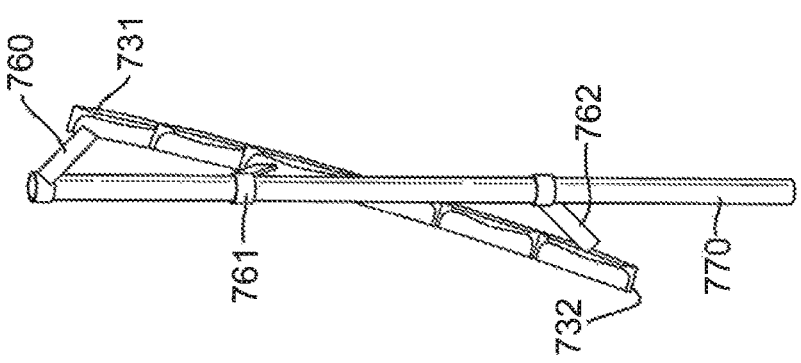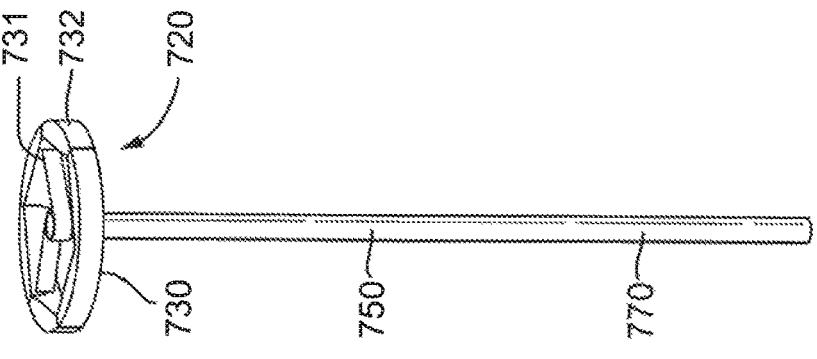

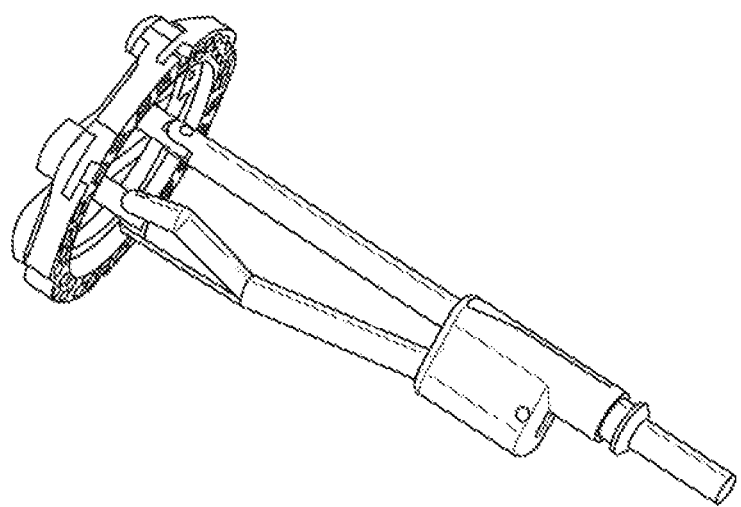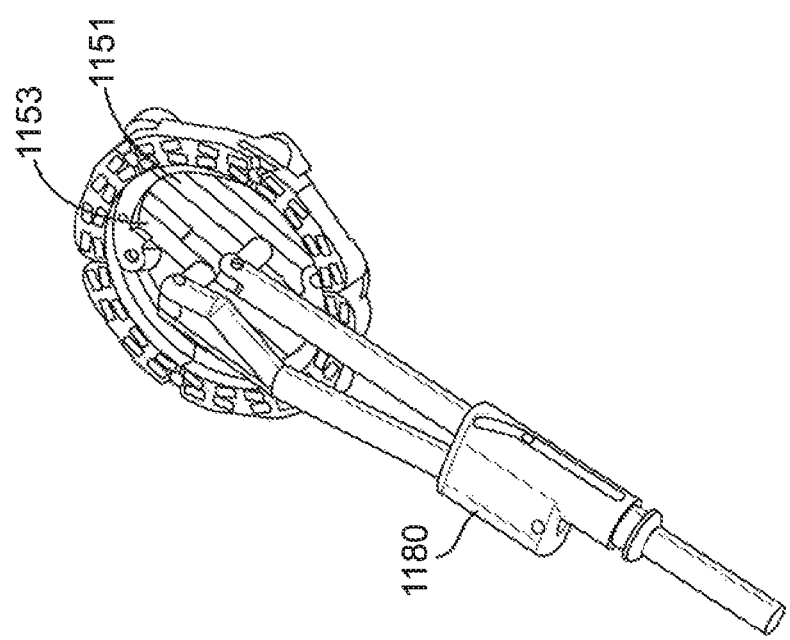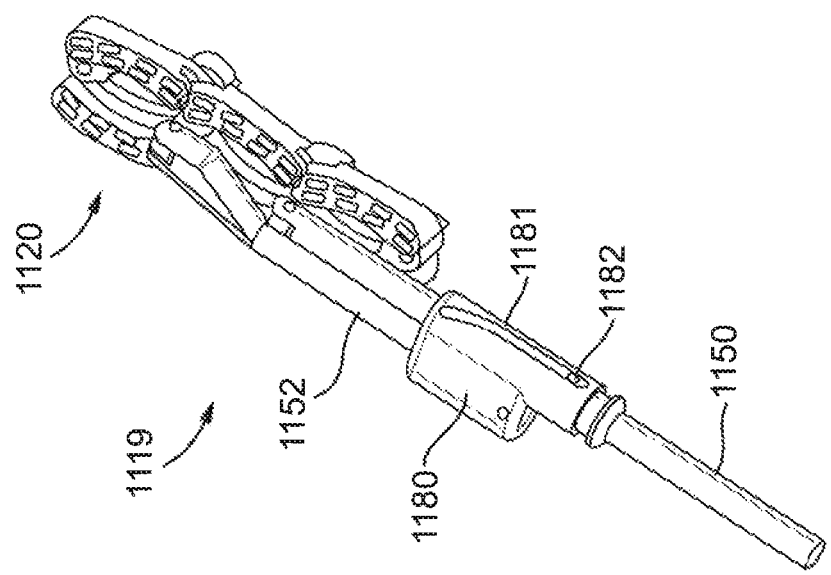

SURGICAL STAPLER, ANVIL FOR A SURGICAL STAPLER, AND A METHOD OF STAPLING TISSUE

TECHNICAL FIELD

The present invention relates to a surgical stapler, an anvil for a surgical stapler and methods of stapling tissue, in particular human or animal tissue.

BACKGROUND OF THE INVENTION

During some surgical methods it is desirable or necessary to staple tissues together. In particular, it can be necessary to staple the ends of two closed tubes in the body together to form one tube. This may be the case where a section of a tube (such as a section of the gastrointestinal tract, which includes the oesophagus, stomach, duodenum, jejunum, ileum, colon and rectum) has been removed from the body. This may have occurred for instance when cancerous tissue is removed. The tube either side of the removed section is typically closed, for example by staples or stitches. After the section of the tube is removed, it is necessary to join the two closed portions of the tube together.

A prior art example of a stapler designed to join to tube portions together is shown in FIG. 1. This shows a prior art stapler 1 and anvil 20 that are used to connect two tubes of the body together. The stapler 1 is inserted into a tube 10 from a proximal end 12. The anvil 20 is inserted into a tube 11 from the distal end 13. Thus, to staple the two tubes 10, 11 together, access is required from two sides 12, 13.

During stapling, the anvil 20 and the stapler 1 are pressed toward each other. This draws the closed ends 14, 15 of the two tubes 10, 11 towards each other. When the anvil 20 presses against stapler 1, and the tissue of the ends 14, 15 of the tubes 10, 11 are effectively clamped between the stapler 1 and the anvil 20, the stapler 1 can fire staples toward the anvil 20 and hence through said tissue. The anvil 20 provides resistance to said staples and hence aids in their folding. Once folded, the staples hold the two tubes 10, 11 together. The stapler 1 and anvil 20 are circular and produce a double concentric ring of staples.

The stapler 1 comprises a circular knife edge (not shown) that is then pressed against the anvil 20 inside the ring of staples. This cuts through the ends 14, 15 of the tubes 10, 11, thus forming a path between the tubes 10, 11. The stapler 1 is then removed from the proximal end 12 and the anvil is also removed from the proximal end 12. The anvil 20 is first tilted and then pulled through the path between the tubes 10, 11.

As can be appreciated, this method requires access from both the proximal end and the distal end to the region to be stapled.

Various proposed alternatives to the standard prior art technique of FIG. 1 are disclosed in US 2015/0327853. In some embodiments, this document discloses a surgical stapler that can be inserted and operated from only the proximal end. This is achieved by the surgical stapler comprising an anvil whose area can be decreased when being inserted through the tissue to be stapled and when being retracted through the tissue after stapling and whose area can be increased during the stapling operation to provide resistance to the staples. An 'umbrella' type collapsing mechanism is used. However, the decreased area is still relatively large and it is therefore difficult to insert the anvil through the tissue to be stapled, and the anvil can cause damage to the staples when it is retracted through the stapled tissue. In other embodiments of US 2015/0327853 the collapsing mechanism involves a folding disc or segments of a ring that join together to form the anvil, which allows for a smaller size for the folded anvil. However, in those cases there is a requirement for access to the anvil from the distal end, i.e. beyond the stapling location, which complicates the surgical procedure, and there is in some cases no straightforward way to collapse the anvil after use, which means that the risk of damage to the stapled tissue is no lower than for the conventional anvil FIG. 1.

SUMMARY OF THE INVENTION

In a first aspect the invention provides, a surgical stapler comprising: a proximal end and a distal end, wherein the proximal end is proximate to the user in use and the distal end is distal from the user in use; an anvil at the distal end for providing resistance to staples during the stapling operation of the surgical stapler, wherein the anvil is configured to be actuated between a deployed state and a collapsed state, wherein the anvil comprises a plurality of segments arranged end-to-end, wherein the anvil is elongated in the collapsed state, the anvil being elongated generally in a first direction, wherein when viewed along the first direction the area covered by the anvil is greater in the deployed state than the collapsed state, wherein the anvil is configured such that the segments rotate about a rotation axis along a second direction perpendicular to the first direction when the anvil is actuated between the deployed and the collapsed states, and wherein the anvil is configured such that adjacent segments pivot relative to each other about a pivot axis along a third direction perpendicular to the second direction when the anvil is actuated between the deployed and collapsed states; and an actuator mechanism configured to actuate the anvil between the deployed and collapsed states, wherein the actuator mechanism is configured to be controlled from a location on the surgical stapler towards the proximal end.

Since the anvil is in an elongated state when in its collapsed stated, and can expand to cover a larger area by the rotating and the pivoting actions when in its deployed state, the surgical stapler can provide a less traumatic way for providing the anvil in the necessary location for stapling and for removing the anvil, together with the stapler, after stapling. In comparison with the majority of known staplers, trauma is reduced since the anvil is part of the stapler itself and can be inserted into the body with, and can be actuated by, the stapler itself. In comparison with the stapler of US 2015/0327853 discussed above, due to the segment design of the anvil and the rotating and pivoting action of the segments, the size of the hole in the tissue required to insert and remove the anvil may be significantly smaller. This reduces the intrusiveness of the insertion of the anvil, reduces possible trauma when removing the anvil and reduces the chances of disrupting the staples when removing the anvil. The rotating and pivoting motion can also be implemented easily with control of the actuator mechanism to collapse and/or expand the anvil from a location towards the proximal end, without the need for accessing the anvil from the distal end, i.e. beyond the stapling location, as in some of the proposed prior art arrangements.

The anvil may be located generally proximate to the distal end of the surgical stapler. The anvil may be located at, or may be, the very end of the distal end of the surgical stapler. The anvil may extend over a certain length of the surgical stapler, particularly when in the collapsed position. The anvil may protrude from a body of the stapler, such as a stapler head. The anvil may be retractable into (and extendable out from) a body of the stapler, such as a stapler head.

The anvil is actuated by the actuator mechanism.

The actuator mechanism may comprise a tensioning system configured to apply tension to the anvil. Preferably, when tension is applied to the anvil, the anvil may be actuated from the collapsed state to the deployed state. When tension is not applied (or released), the anvil may collapse into the collapsed state, preferably automatically. Alternatively, when tension is applied to the anvil, the anvil may be actuated from the deployed state to the collapsed state. When tension is not applied (or released), the anvil may deploy into the deployed state, preferably automatically. The tension mechanism may comprise the handle of the anvil assembly discussed below.

The actuator mechanism may comprise the two shafts that can move relative to one another discussed further below.

When there are two shafts present, the actuator mechanism of the stapler may be able to actuate move the two shafts relative to each other to cause the actuation. This may be achieved by applying tension or a pushing force to the bracket.

When there is a handle present in the anvil assembly, the actuator mechanism of the stapler may be able to apply a tension to the handle to cause the actuation.

In the collapsed state, all adjacent segments of the anvil may be physically attached or fixed to each other. In the deployed state, all adjacent segments of the anvil may be physically attached or fixed to each other, or all but one pair of adjacent segments of the anvil may be physically attached or fixed to each other. By physically attached or fixed, it means there is some attaching means, such as a hinge mechanism, which would prevent the adjacent segments becoming separated if they were pulled apart.

The tensioning system may comprise an actuating line, such as a wire or string or cable, passing through each of the segments. However, it may be fixed to the distal-most segment.

The actuator line may be free to move relative to each of the segments it passes through. However, when tension is applied, the actuator line may cooperate with the distal-most segment such that the tension in the actuator line pulls the distal-most segment toward the other segments, thus acting to compress the segments. The segments may be shaped such that when this tensioning occurs, the anvil changes from its collapsed to its deployed state.

The elongated shape of the anvil in the collapsed state may be such that the length of the anvil in the first direction is longer than its length in any other direction. The dimension of the anvil in the first direction may be longer than the dimension of the anvil in any other direction. Preferably, when in the collapsed state, the ratio of the length of the anvil to its width (in a direction perpendicular to the length) is at least 2:1, preferably at least 3:1, preferably at least 4:1, preferably at least 5:1, preferably at least 10:1. Further, when in the collapsed state, the ratio of the length of the anvil to its depth (in a direction perpendicular to the length and width) is at least 2:1, preferably at least 3:1, preferably at least 4:1, preferably at least 5:1, at least preferably 10:1. Any combination of these width and depth ratios may be possible. Due to the segmented, rotating nature of the anvil, larger ratios are possible here than for prior art anvils, which reduces the size of the hole required for the collapsed anvil to extend through, and hence reduces the necessary trauma to tissues.

The first direction is a linear direction and is generally defined by the direction in which the elongated collapsed anvil extends. Preferably, the first direction may also be thought of as being a general direction from the proximal end to the distal end of the surgical stapler. The stapler may have an axial direction extending from the proximal end to the distal end. The axial direction may be a central longitudinal axis of the stapler. The axial direction may be straight or may be curved. The axial direction may be in the first direction, at least at and/or towards the distal end. Having the elongated collapsed anvil extending in the general direction between the proximal and distal ends can improve the control of the stapler when inserting the anvil through tissue during the stapling process, and can ease the insertion into the body and removal from of the surgical stapler.

Of course, the elongated shape and the first direction need not be totally aligned. For instance, the direction of the longest dimension of the anvil when in the collapsed shape may be within 30°, within 20° or within 10° of the first direction. What is important is that the area and/or width and/or depth of the collapsed anvil when viewed along the direction in which the collapsed anvil is moved through the tissue (e.g. the first direction) is small (preferably as small as possible) so that when the anvil is moved through tissue the hole required for the anvil is as small as possible.

The anvil may consist of two to fifteen segments, preferably three to ten segments, preferably four to eight segments, preferably four segments or six segments.

During actuation, each segment may rotate and pivot. In some examples, most of the segments, preferably all of the segments, may rotate by the same amount about the axis in the second direction during actuation between the deployed and the collapsed state. In other examples there is a varying degree of rotation and/or different directions of rotation. In some examples, most of the segments, preferably all of the segments, may pivot by the same amount relative to each other during actuation between the deployed and the collapsed state. In other examples there is a varying degree of pivoting and/or different directions of pivoting.

Each segment may have a length, which is generally oriented in the elongated direction of the anvil in the collapsed state, and may be orientated generally perpendicular to the first direction when in the deployed state. Each segment may be generally elongated (even if it is curved) and the length may be generally in the direction of said elongation.

Each segment may have a width. The width may be generally perpendicular to the length. The width of each segment may define the surface for providing resistance to the staples during the stapling operation. The width should therefore be sufficiently large to provide a large enough area to provide resistance to the staples during the stapling operation.

Each segment may have a depth. The depth may be generally perpendicular to the length and the width. The depth may be sufficient for providing adequate strength and rigidity to the anvil for providing resistance during the stapling operation. The depth direction may be orientated generally in the first direction when the anvil is deployed.

Each segment may comprise two ends, one at each end of the length of the segment. These ends may comprise respective end surfaces.

The segments may be shaped such that when the anvil is in its deployed state, the segments form a rigid anvil. The segments may be shaped such that when the anvil is in its deployed state, then the end surfaces of the adjacent segments abut each other. This abutment may be such that there is more end surface contact between adjacent segments when the anvil is deployed than when the anvil is collapsed.

Further, as mentioned above, there may be a force present (such as tension and/or compression) that forces the segments in a way that increases the contact and/or friction between the end surfaces of adjacent segments, but does not cause any movement of the segments due to their shape—the segments are shaped to provide a reaction force. Thus, the segments may be stressed when in the deployed state, and may preferably be held against movement (despite the force being present) by the shape of each segment causing an interaction between the end surfaces of neighbouring segments, which provides the reaction force and hence maintains the stressed state.

For instance, some or all of the segments may be at least partially curved. For instance, they may be or comprise crescent or arc-shapes. An arc-shape may be an arc of a circle, an oval or an ellipse. The segments may be curved such that they collectively may form a substantially continuously curved shape (such as a circle, an ellipse, an oval or a stadium) when the anvil is deployed. Such a shape allows for a curved anvil when deployed, which can reduce the stress on body tissues and can be particular strong under compression/stress.

It may be the outermost periphery of the segments (when in the deployed state) that are curved. The innermost periphery of the segments (when in the deployed state) may also be curved, or may be straight.

The ends of the segments may be perpendicular to the direction of the curve (e.g. the tangent of the curve) of the segment at the respective ends of the segment, e.g. when the segment is an arc of a circle, the ends may extend in the radial direction of said circle.

Alternatively, the ends of the segments may be at an angle between perpendicular to the direction of the curve (e.g. the tangent of the curve) and the direction of the curve (e.g. the tangent of the curve) of the segment at the respective ends of the segment. Preferably the ends extend in a direction between 45°-90° from the direction of the curve, preferably 60°-90°, preferably 80°-90°.

Alternatively/additionally, some or all of the segments may be at least partially straight. The segments may be straight such that they collectively may form a polygon when the anvil is deployed. The polygon may have at least four sides (e.g. a rectangle), but preferably has at least five sides (e.g. a pentagon), at least six sides (e.g. a hexagon), at least eight sides (e.g. an octagon), at least ten sides (e.g. a decagon) or at least twelve sides (e.g. a dodecagon). The corners of the polygon may be where adjacent segments meet one another. There may be only one segment per side.

It may be the outermost periphery of the segments (when in the deployed state) that are straight. The innermost periphery of the segments (when in the deployed state) may also be straight, or may be curved.

The end surfaces of the segments may extend toward the centre of the polygon when the anvil is deployed.

Adjacent segments may pivot relative to each other about a pivot point. The pivot point may be a hinge. The pivot point may be located where the end of one segment meets the end of an adjacent segment, when the anvil is in the collapsed state. In the collapsed state, this may be the only the location at which said ends meet—the remainder of the ends may be spaced from one another due to the shape of the respective segments (e.g. the angle of their end surfaces). Thought of in an alternative way, the segments may be described as being articulated, such that they are held together but are allowed to pivot relative to each other.

At least one or each of the segments may comprise a cutaway portion. The cutaway portion may be shaped such that the segment(s) can be more closely fit to the shaft (see below) when the anvil is in the collapsed state, which helps to minimise the area of the collapsed anvil.

At least one of the segments may comprise a pin. At least one of the segments may comprise a notch for accepting the pin. The pin and the notch may be arranged such that they engage with one another when the anvil is in the deployed state. This engagement may provide some additional strength to the deployed anvil and may prevent the anvil incorrectly collapsing.

In the deployed state the anvil is preferably a ring-shape. The ring may preferably be (substantially) continuous. By substantially continuous, it is meant that the ring is at least largely complete, but there may be some minor break(s) in the ring. For example, a distal end of an end segment of the anvil (e.g. at the most distal end of the anvil when in the collapsed state) may not physically be attached/secured to its adjacent segment when in the deployed ring shape. However, it may be pressed against said adjacent segment by compression forces.

The ring may be curved, such as a closed curve, such as a circle, an ellipse an oval or a stadium. This is an advantage since it is usually desirable to staple tissue in as continuously curved a manner as possible, to avoid stressing tissue by sharp corners. Further, the curve may provide added strength when the anvil is deployed (e.g. under stress). However, it is also possible for the ring to be a polygon, which may be easier to manufacture. If enough corners are present, such as in a pentagon, a hexagon, a heptagon, an octagon, a nonagon or a dodecagon, etc., then the stress on the tissue caused by the corners may not be overly great. Moreover, the anvil may be a polygon that holds a curved element for interaction with a ring of staples during the stapling operation of the surgical stapler.

The curve here may preferably refer to the outermost periphery of the ring. The innermost periphery of the ring may be straight and/or curved.

In the deployed state, the anvil may alternatively be disc-shape or a dome-shape. The disc or dome may preferably be (substantially) continuous. By substantially continuous, it is meant that the dome or disc is at least largely complete, but there may be some minor break(s) in the dome or disc. For example, a distal end of an end segment of the anvil (e.g. at the most distal end of the anvil when in the collapsed state) may not physically be attached/secured to its adjacent segment when in the deployed dome or disc shape (however, it may be pressed against said adjacent segment by compression forces).

The dome or disc may have a curved periphery and may be a generally solid shape (i.e. there may be no large hole in the centre, unlike the ring). The periphery may be shaped like a circle, an ellipse an oval or a stadium. A curved shape is preferable since it is usually desirable to staple tissue in as continuously curved a manner as possible, to avoid stressing tissue by sharp corners. Further, such a curved shape may provide added strength when the anvil is deployed (e.g. under stress). However, it is also possible for the disc or dome to be a polygon, which may be easier to manufacture. If enough corners are present, such as in a pentagon, a hexagon, a heptagon, an octagon, a nonagon or a decagon, etc., then the stress on the tissue caused by the corners may not be overly great.

When the anvil is a disc, the anvil may be planar in its deployed state.

When the anvil is a dome, the dome may have at its peak the distal end of the shaft (see below). This distal end may be a flared or enlarged end, in comparison to the remainder of the shaft. The distal end may meet with inner surfaces of the segments to form the dome. The segments may slope down away from the distal end toward the proximal end with increasing radial distance from the shaft.

Preferably at least some of the segments are orientated such that they extend (e.g. the direction from one end of a segment to the other end of the same segment) substantially perpendicular to the first direction when the anvil is deployed. Of course, the segments need not be totally perpendicular to the first direction. For instance, the segments may extend 60-90°, 70-90° or 80-90° from the first direction. What is important is that the area the anvil is increased in comparison to the small area of the collapsed state. Further, it is important that the anvil provides a suitable surface for providing resistance to the staples in stapling operation.

When the anvil is deployed, the segments of the anvil may define a plane. This plane preferably has a normal within 30°, within 20° or within 10° of the first direction. Preferably, the normal is substantially parallel with the first direction. The plane may be defined by the orientation of the segments, e.g. the plane in which the segments lie, e.g. the plane in which the curve or ring or dome or disc lies.

The area covered by the anvil may be the area defined by the outer periphery of the anvil when in the deployed state. For instance, it may be the area defined by the outer perimeter of the ring. Of course, the actual area provided by the anvil for providing resistance to staples may be smaller than the area covered by the anvil, since not all of the area covered by anvil may provide resistance to staples since there may be gaps (e.g. the area of an annulus is smaller than the area of a circle).

Preferably, the area covered by the anvil in the deployed state in comparison to the collapsed state is at least 2, 4, 6, 8, 10 or 20 times greater.

The rotation of the segments about a rotation axis in the second direction may be thought of as a re-orientation of the segments between the collapsed and deployed states. The rotation may be of the general length-direction of the segments. For instance, in the collapsed state, the length-direction of the segments may generally be in the first direction. However, during deployment this length-direction rotates about an axis in the second direction. Thus, in the deployed state, the length-direction of the segments may not be in the first direction. Preferably, the length-direction of the segments is rotated to be 60-90°, 70-90°, 80-90°, or substantially 90° to the first direction.

Each of the segments may rotate by substantially the same amount about the rotation axis in the second direction between the collapsed and the deployed states.

The pivoting of the segments relative to one another about a pivot axis in the third direction may be thought of as a re-orientation of the segments relative to one another between the collapsed and deployed states. The pivoting may be of the general length-direction of the segments. For instance, in the collapsed state, the length-directions of the segments may generally be in the first direction, and hence may be generally parallel and colinear with each other. However, during deployment this length-direction rotates about an axis in the third direction. Thus, in the deployed state, the length-directions of respective segments may not be parallel with each other. Rather, they pivot and are non-parallel with each other. Preferably, in the collapsed state, the length-directions of respective segments are within 0-30°, 0-20°, 0-10°, or substantially 0° to each other. However, in the deployed state, the length-directions of the adjacent segments may be 30-90°, 45-90°, 60-90° to each other. For instance, when six segments make up a ring, adjacent length-directions are substantially 60° to each other.

Each of the segments may pivot relative to their adjacent segment(s) by substantially the same amount between the collapsed and the deployed states. However, it is also possible, depending on the collapsed configuration of the segments, to have different pivoting angles.

When in the deployed state, the anvil may have a direction of curvature. This is present when the segments are curved. For instance, when the anvil is circular, the direction of curvature is towards the centre of the circle. However, a direction of curvature may also be present when the segments are straight. For instance, a polygon may be thought of as having a general direction of curvature inwards toward the centre of the polygon.

At least two adjacent segments may pivot relative to each other in an outward direction relative to the direction of curvature when the anvil changes from the deployed state to the collapsed state. Thus, the at least two adjacent segments may pivot relative to each other in an inward direction relative to the direction of curvature when the anvil changes from the collapsed state to the deployed state. The two adjacent segments that pivot outward relative to each other may pivot by less than or equal to 90°. For instance, when n segments are present, the outward pivot may be substantially equal to 360°/n.

In addition to this, in some embodiments, at least two adjacent segments may pivot relative to each other in an inward direction relative to the direction of curvature when the anvil changes from the deployed state to the collapsed state. Thus, the at least two adjacent segments may pivot relative to each other in an outward direction relative to the direction of curvature when the anvil changes from the collapsed state to the deployed state. The two adjacent segments that pivot inwards relative to each other may pivot by more than or equal to 90°. For instance, when n segments are present, the inward pivot may be substantially equal to 180°-360°/n. There may preferably be (only) two pairs of adjacent segments that pivot inwardly. This may be the case where the ring collapses into two collapsed ring halves, as discussed below.

However, in other embodiments, all adjacent (physically attached) segments may pivot relative to each other in an outward direction relative to the direction of curvature when the anvil changes from the deployed state to the collapsed state. This may be the case where the ring collapses into one linear arrangement of segments, as discussed below. Thus, the all adjacent segments may pivot relative to each other in an inward direction relative to the direction of curvature when the anvil changes from the collapsed state to the deployed state. The two adjacent segments that pivot outward relative to each other may pivot by less than or equal to 90°. For instance, when n segments are present, the outward pivot may be substantially equal to 360°/n.

Whilst the location of the axis of the pivot may different for each adjacent pair of segments (the axis of the pivot will be located at a pivot point, such as a hinge, located where two adjacent segments meet), every pivot axis may be in the same direction (the third direction).

The third direction may change relative to the first direction, since the third direction will rotate as the segments rotate about the axis in the second direction. For instance, when the length-direction of the segments is in the first direction (e.g. when the anvil is in the collapsed state) the third direction may be perpendicular to the first direction. However, if the segments are rotated by 90° about the axis in the second direction, the third direction may be substantially parallel to the first direction.

The actuator mechanism may comprise a rotation actuator and a pivoting actuator. In some cases, the rotation actuator and pivoting actuator may be the same actuator. As has been discussed above, the actuator mechanism may include an actuator line, such as a string, wire or cable, that is used to provide tension to the segments, thus drawing the segments towards each other, thus rotating and pivoting the segments due to the shape of the segments and the contact of adjacent segments. The actuator mechanism may include the two shafts that can move relative to one another discussed below.

However, additionally/alternatively, other types of actuator elements can be used. For instance, the anvil can be biased to be in the deployed state, e.g. via some resilient component, such as a spring. Preferably, however, the anvil may be biased to be in the collapsed state, e.g. via some resilient component, such as a spring. The actuator mechanism may work against such a biasing during actuation in one direction and may allow (or work with) the biasing to have effect during actuation in the other direction. The anvil may additionally/alternatively be actuated by a transmission system, such as a transmission system comprising a rotating member (such as a shaft and/or gears), whose rotation can be transferred to the rotation and pivoting motion of the segments.

As mentioned above, the anvil may be actuated using two shafts. A first of the shafts may be the shaft discussed herein in relation to the anvil assembly and/or the stapler. A second of the shafts may be an additional second shaft that is moveable relative to the first shaft to actuate the anvil. This motion of the second shaft may be a sliding motion relative to the first shaft along the first shaft, a rotation about the first shaft, and/or a pivoting away or toward the first shaft.

The first shaft may be attached to a first support arm, which in turn may be attached to segments of the anvil (preferably to at least one pivot point where to adjacent segments meet). The first support arm may be able to rotate relative to the first shaft about the axis in the second direction. The first support arm may or may not be able to pivot relative to the first shaft about the axis in the third direction.

The second shaft may be attached to a second support arm, which in turn may be attached to segments of the anvil (preferably to at least one pivot point where to adjacent segments meet). The second support arm may be able to rotate relative to the second shaft about the axis in the second direction. The second support arm may or may not be able to pivot relative to the second shaft about the axis in the third direction.

The second shaft may be connected to the first shaft. This may occur through the use of a bracket. The second shaft may slide (in the first direction) relative to the first shaft. The second shaft may rotate about the first shaft when it slides. The second shaft may pivot relative to the first shaft (such that the second shaft can alternate between being completely parallel with the first direction and being off-parallel with the first direction).

These relative movements may be achieved by the use of the bracket. The bracket and/or the first shaft may comprise a curved groove, and the other of the bracket and/or first shaft may comprise a peg that slides in the groove. The second shaft may also be housed in the bracket such that the pivoting movement on mentioned above is allowed.

Thus, when in the collapsed state, the first and second shafts may be parallel with one another and may be close to one another (preferably in contact). To actuate the anvil, the second shaft may be moved relative to the first shaft, such that it slides relative to the first shaft. Due to the groove and peg arrangement in the bracket, this sliding motion also causes the second shaft to rotate relative to the first shaft. Due to these two motions, the second shaft may move away from the first shaft, and may pivot relative to the first shaft such that the second shaft is no longer totally parallel with the first shaft.

Due to these combinations of motions, and due to the presence of the first and second arms connecting the first and second shafts to the anvil segments (the first and second arms being able to rotate and possible pivot relative to the first and second respective shafts and being able to pivot relative to the segments of the anvil, as discussed above), the anvil may be actuated from its collapsed state to its deployed state (or vice versa).

The proximal end of the second shaft may terminate at the bracket. The first shaft may pass through the bracket.

At or toward the proximal end of the stapler, the stapler may comprise a user interface, such as a handle. The user interface may be connected to the actuator mechanism and may allow the user to control the actuator mechanism.

The present stapler can perform a stapling operation by accessing the tissue to be stapled from only one direction, i.e. there is no need to access the area from a second opposite direction to provide resistance to the stabling operation. This is achieved by having the above-described anvil incorporated into the stapler.

The surface of the anvil that faces the proximal direction when deployed may be thought of as a stapling surface. The stapling surface is suitable for providing resistance to the staples in stapling operation. The stapling surface may be a surface that contacts the tissue and provides resistance to the staples piercing through the tissue during the stapling operation. The stapling surface may be the same general shape as the deployed anvil (e.g. ring-shaped or annular, etc.).

The stapling surface may comprises a plurality of recesses. The recesses may be shaped and positioned on the surface so as to interact with the staples piercing through the tissue so as to assist with the folding of the staples. There may be one recess per stapler head opening (see below), and each recess may be located on the surface so as to interact with a staple coming from a respective opening.

The recesses may be arranged in a ring, corresponding to the ring shape of the deployed anvil and the ring shape of the stapler head openings. The recesses may be arranged in two concentric rings, corresponding to the two concentric rings of the openings of the stapler head.

When deployed, the anvil may comprise a cutting surface that faces toward the proximal end. The cutting surface may be a surface that contacts the tissue and provides resistance to a sharp edge (which may be part of the stapler, see below) that cuts through the tissue during the stapling operation. The cutting portion may comprise a resilient material, such as rubber or plastic. The resilient material may aid the cutting process.

The cutting surface may be in the shape of a ring or annulus. Preferably the cutting surface may be radially inward of the stapling surface.

The shape of the cutting surface (e.g. the radius and thickness of the annulus) may be such that the sharp edge (discussed in more detail below) contacts only the cutting surface during the cutting operation.

The anvil may comprise a recess in which the material that forms the cutting surface is housed.

The cutting surface may be formed of segments. There may be one segment of the cutting surface for each respective segment of the anvil. The segments of the anvil may each comprise a recess in which respective segments of the cutting surface are housed. These recesses are preferably toward the radially inner portion of the anvil segments.

The segments of the cutting surface may be fixed to the respective anvil segments. The segments of the cutting surface may be configured to rotate and pivot with the respective anvil segments when the anvil is deployed or retracted.

The segments of the cutting surface may pivot relative to one another just as the respective segments of the anvil pivot relative to one another. To allow for this pivoting, the ends of the segments of the cutting surface comprise cutaway portions that allow for the pivoting whilst forming a complete cutting surface when the anvil is deployed.

The anvil may comprise a peripheral protective portion. This may be located at the periphery of the anvil, such as at the outermost portion of the ring. The protective portion may define the outer circumference or periphery of the anvil. The protective portion may be ring-shaped and may be thought of as an outer ring of the anvil. The protective portion may be located on or attached to the outer edge of the anvil ring. The protective portion may be flexible and/or elastic, and may be made from rubber. This allows the protective portion to collapse and deploy with the anvil segments to which it is attached when the anvil is collapsed and deployed. The protective portion is for protecting the tissue local to anvil from being caught in the moving parts of the anvil (such as between the segments), which may otherwise occur during deployment or collapse of the anvil, or at another time.

The stapler may also comprise a shaft. The shaft may be elongated. The shaft may be located at or toward the distal end of the stapler. The shaft may extend toward the proximal end, and may extend into the stapler head. The shaft may comprise or contain at least part of the actuator mechanism. At least at or toward the distal end, the shaft may extend generally in the first direction. The shaft may be located at a central longitudinal axis of the stapler. The shaft may be substantially rigid and inflexible, i.e. it does not rotate or pivot like or with the anvil segments; rather, it may remain stationary relative to the remainder of the stapler during actuation of the anvil. The shaft is preferably not segmented.

The anvil may be attached to the shaft, preferably to the distal end of the shaft, e.g. within 10 cm, 5 cm, 2 cm or 1 cm of the very distal end of the shaft. Alternatively, the shaft of the anvil assembly (see below) may be attached to the shaft of the stapler. In this case, when the anvil assembly is attached to the shaft of the stapler, the shaft of the anvil assembly and the shaft of the stapler may effectively form one continuous shaft that is preferably linear.

Any reference to the shaft below may be a reference to the shaft of the stapler, or the shaft of the anvil assembly, or the continuous shaft formed by the shaft of the stapler and the shaft of the anvil assembly.

When in the deployed state, the anvil may be attached (only) to the very distal periphery of the shaft (which may be the shaft of the anvil assembly, or the shaft of the stapler, or the continuous shaft formed by the shaft of the anvil assembly and the shaft of the stapler). When in the collapsed state, the anvil may be attached (only) to the very distal periphery of the shaft (which may be the shaft of the anvil assembly, or the shaft of the stapler, or the continuous shaft formed by the shaft of the anvil assembly and the shaft of the stapler). However, it may also be attached at a location on the shaft (which may be the shaft of the anvil assembly, or the shaft of the stapler, or the continuous shaft formed by the shaft of the anvil assembly and the shaft of the stapler) toward the proximal end of the stapler, but still proximate the distal end.

The anvil may be attached to the shaft (which may be the shaft of the anvil assembly, or the shaft of the stapler, or the continuous shaft formed by the shaft of the anvil assembly and the shaft of the stapler) by one or more supporting arms.

The supporting arm(s) may connect to the shaft, preferably the very distal end of the shaft. The supporting arm(s) may connect to the anvil.

When the anvil is a ring-shape, the supporting arm (s) may be arranged such that the shaft is within the area covered by the ring when viewed along the first direction, preferably the shaft is toward the centre of the ring.

Preferably, when the anvil defines a plane in its deployed position, the supporting arm (s) may be at least partially substantially in said plane.

The supporting arm (s) may comprise segments, similar to those of the anvil. The segments of the supporting arm (s) may be shaped such than when the anvil is actuated, the supporting arm is also actuated by the actuator mechanism such that the supporting arm acts to position the anvil in the correct position and orientation.

When in the collapsed state, the supporting arm (s) may be orientated substantially parallel to the first direction. When in the deployed state, the supporting arm (s) may be orientated at least partially perpendicular to the first direction.

The supporting arm (s) may have fixed lengths, e.g. the length of the or each supporting path does not change during actuation, i.e. it is the same in the deployed and collapsed states.

When there is a plurality of supporting arms, each supporting arm may have the same length.

A casing may be provided in which the shaft (which may be the shaft of the anvil assembly, or the shaft of the stapler, or the continuous shaft formed by the shaft of the anvil assembly and the shaft of the stapler), the anvil and/or the supporting arms can be held, for example during insertion through a small hole in the tissue. The casing may be cylindrical and may be part of the stapler.

In some embodiments, the anvil may be attached to the shaft by only one supporting arm. This may be advantageous as it allows a simple attachment. This supporting arm may be segmented as discussed above.

In the collapsed state, the shaft (which may be the shaft of the anvil assembly, or the shaft of the stapler, or the continuous shaft formed by the shaft of the anvil assembly and the shaft of the stapler), the supporting arm and the anvil may all extend substantially in the first direction, co-linearly in an end-to-end fashion. However, in the deployed state, the supporting arm may act as a spoke between the deployed anvil and the shaft.

In other embodiments, the anvil may be attached to the shaft (which may be the shaft of the anvil assembly, or the shaft of the stapler, or the continuous shaft formed by the shaft of the anvil assembly and the shaft of the stapler) by a plurality of supporting arms. For instance, there may be (only) two, three or four supporting arms. Having a plurality of supporting arms is particularly advantageous as it provides additional support to the anvil, which is beneficial since the anvil is required to provide sufficient resistance to staples during the stapling operation. When the deployed anvil is a ring shape, the supporting arms may support opposite sides of the ring. For instance, when there are two supporting arms, these may be spaced around the ring by around 180°. When there are four supporting arms, these may be spaced around the ring by around 80-100°, preferably 90°. The supporting arms may be rotationally symmetrically arranged around the ring.

Each supporting arm may be substantially the same length. This allows the shaft to be located toward the centre of the ring.

At least one (or each) supporting arm may extend between the shaft and one of the segments of the ring. The supporting arm may attach to a point distant from either end of said segment, e.g. proximate to the midpoint along the length-direction of the segment. This allows for a strong attachment between the segment and the supporting arm, and hence allows for improved rigidity. When this occurs, a pivot may be provided to connect the supporting arm to the segment, to allow the segment to pivot relative to the supporting arm during actuation of the anvil.

Alternatively, at least one (or each) supporting arm may extend between the shaft and the location between adjacent segments of the ring. This allows for the possibility of using the same pivot point (e.g. hinge) for allowing the anvil to pivot relative to the supporting arm(s) as is used for allowing adjacent segments to pivot relative to each other. However, it does mean that the length of the supporting arm may need to be longer in the collapsed state than in the deployed state (or vice versa). Thus, a curved or flexible supporting arm can be used. Such a supporting arm may be inflexible/rigid in the third direction but may be flexible perpendicular to the third direction.

The (or each) supporting arm may pivot relative to the segments of the anvil about an axis (or axes) that are orientated in the third direction.

To actuate the pivoting of the (or each) supporting arm relative to the segments, the actuator line may connect between the supporting arm and the segments. The actuator line may be arranged such that when it is tensioned (e.g. by action from the user at the proximal end of the stapler), the supporting arm may pivot relative to the segments. This in turn may cause the adjacent segments to pivot relative to each other. This (possibly in combination with a suitable biasing) may drive the anvil between the deployed and collapsed states.

For instance, the actuator line may connect between the supporting arm and the anvil. A respective actuator line may extend between a plurality of the supporting arms (or each supporting arm) and the anvil, preferably to the segment to which the respective supporting arm is attached. The actuator line may extend between the supporting arm and the anvil at an angle relative to the supporting arm. This means that when the actuator line is tensioned, the supporting arm may be pivoted relative to the anvil, and hence the anvil may collapse.

In the collapsed state, the shaft (which may be the shaft of the anvil assembly, or the shaft of the stapler, or the continuous shaft formed by the shaft of the anvil assembly and the shaft of the stapler), the supporting arm and the anvil may all extend substantially in the first direction, however the anvil and the supporting arms may be parallel to, but radially offset from, the shaft. The radial offset may be small, preferably as small as possible, such as the supporting arms and/or the anvil may be touching the shaft. Thus, at least some of anvil and supporting arms may be gathered alongside the shaft (i.e. they may overlap with the shaft in the first direction).

In the collapsed state, a first portion of the anvil and/or the supporting arm(s) may overlap with the shaft (which may be the shaft of the anvil assembly, or the shaft of the stapler, or the continuous shaft formed by the shaft of the anvil assembly and the shaft of the stapler) in the first direction, and a second portion of the anvil and/or the supporting arm(s) may extend beyond the distal end of the shaft in the first direction. The first portion may be called an overlapping portion and the second portion may be called an extending portion. The anvil and the supporting arms may consist of the first and second portions. The first and second portions may be symmetric halves of the anvil and supporting arms.

In the deployed state, the supporting arms may all connect to the shaft (which may be the shaft of the anvil assembly, or the shaft of the stapler, or the continuous shaft formed by the shaft of the anvil assembly and the shaft of the stapler) toward the end, preferably the very distal end, of the shaft. In the collapsed state, the supporting arms may also all connect to the shaft at a location toward the end, preferably the very distal end, of the shaft.

This connection location may comprise a pivot. The axis of rotation of this pivot may be in the second direction. The anvil (and supporting arms) can therefore rotate about this pivot so as to rotate the segments of the anvil around the axis in the second direction. The pivot may be located proximate the distal end, preferably at the very distal end, of the shaft.

In the deployed state, the anvil may form a ring and the supporting arms may form spokes connecting the ring to the shaft. There may be more than one spoke.

In order to move from the deployed state to the collapsed state, the ring may collapse. This may occur by allowing two pairs of adjacent segments to pivot inwardly with respect to each other (as is described above) and allowing the remaining pairs of adjacent segments to pivot outwardly with respect to each other. The opposite pivoting occurs in the deploying stage (e.g. from collapsed state to deployed state).

The two pairs that pivot inwardly with respect to each other may be substantially 180° opposite each other on the ring. The ring may have even numbers of segments.

For instance, when there are four segments making up the ring, as the ring collapses the first and second segments may pivot inwardly with respect to each other, the second and third segments may pivot outwardly with respect to each other, the third and fourth segments may pivot inwardly with respect to each other, and the fourth and first segments may pivot outwardly with respect to each other. The opposite pivoting occurs in the deploying stage. As another example, when there are six segments making up the ring, as the ring collapses the first and second segments may pivot inwardly with respect to each other, the second and third segments may pivot outwardly with respect to each other, the third and fourth segments may pivot inwardly with respect to each other, the fourth and fifth segments may pivot inwardly with respect to each other, the fifth and sixth segments may pivot outwardly with respect to each other, and the sixth and first segments may pivot outwardly with respect to each other. The opposite pivoting occurs in the deploying stage.

The two pairs of segments that pivot inwardly may be fixed together by a hinge or may be free to both pivot and slide relative to each other.

With such a collapsed ring half of the segments of the ring form a first collapsed half and the remaining segments of the ring form a second collapsed half of the ring. These two collapsed halves may overlap in the first direction in the collapsed state. One of the pivots about which adjacent segments pivot inwards during collapse may be located at the distal end of the collapsed anvil (which is elongated in the first direction) and the other of the pivots about which adjacent segments pivot inwards during collapse may be located at the proximal end of the collapsed anvil.

In one case there may be two supporting arms, optionally no more than two supporting arms. These may take the form of a single member (such as a single bar or plate) whose approximate midpoint is connected to the distal end of the shaft, e.g. at the pivot whose axis of rotation is in the second direction. This single member thus may comprise both supporting arms. The member may connect to two opposite segments, preferably at a location away from the respective ends of both of said segments, e.g. toward the midpoint. The member may be connected to each of the segments by a respective pivot.

In the deployed state, the member may extend in the plane of the ring in a radial direction of the ring. In the collapsed state, the member may extend substantially parallel to the length-direction of the collapsed ring segments, i.e. substantially parallel to the first direction. In the collapsed state, the member may be located in between the two collapsed half rings. Alternatively, the two collapsed half rings may be in contact with each other, and the member may be offset from the two collapsed half rings in the third direction (but preferably still in contact with them).

In another case there may be four supporting arms, optionally no more than four supporting arms. These may take the form of two members whose approximate midpoints are connected to the distal end of the shaft, e.g. at the pivot whose axis is in the second direction. Each of the members thus may comprise two supporting arms. Each member may connect to two different (preferably opposite) segments, preferably at a location away from the respective ends of both of said segments, e.g. toward the midpoint. Each member is connected to each of the segments by a respective pivot.

In the deployed state, the two members may be offset by 45°-90°, preferably 60°-90°, preferably 80°-90°, preferably substantially 90° with respect to each other, about an axis in the first direction.

During collapse, this angle may be reduced to close to 0° such as less than 10°. The members thus pivot relative to each other during collapse. This pivot may be about an axis in the third direction.

The or each member may be straight.

However, alternatively, the or each member may comprise a kink or slight angle. The kink or slight angle may be present at the location where the member is connected to the shaft. Two straight portions of equal length may join at the kink or the slight angle portion.

Alternatively, in the collapsed state, substantially all of the anvil may overlap with the shaft in the first direction. Thus, none (or at least very little) of the collapsed anvil may extend beyond the distal end of the shaft in the first direction.

In the deployed state, the supporting arms may all connect to the shaft toward the end, preferably the very distal end, of the shaft (which may be the shaft of the anvil assembly, or the shaft of the stapler, or the continuous shaft formed by the shaft of the anvil assembly and the shaft of the stapler.

At least one, and preferably all, of the supporting arms may be able to rotate about the shaft (e.g. about an axis in the first direction). During actuation of the anvil, the at least one, and preferably each, of the supporting arms may rotate about the shaft (e.g. about an axis in the first direction).

At least one, and preferably all, of the supporting arms may be able to pivot relative to the shaft (e.g. about an axis perpendicular to the first direction and perpendicular to the direction in which the respective supporting arm extends). During actuation of the anvil, the at least one, and preferably each, of the supporting arms may pivot relative to the shaft (e.g. about an axis perpendicular to the first direction and perpendicular to the direction in which the respective supporting arm extends).

At least one of the supporting arms may be slidable relative to the shaft in the first direction. During actuation of the anvil, the at least one of the supporting arms may slide relative to the shaft (e.g. about an axis in the first direction).

Each of the supporting arms may be able to pivot relative to the anvil.

Each supporting arm may connect between a respective location on the anvil and a respective location on the shaft. Each supporting arm may be connected to a different location on the anvil (such as different segments, or different locations between adjacent segments). In the collapsed state, each supporting arm may connect to the shaft at different positions in the first direction. In the deployed state, each supporting arm may connect to the shaft at substantially the same position in the first direction, e.g. toward or at the distal end of the shaft.

In the deployed state, the anvil may form a ring and the supporting arms may form spokes connecting the ring to the shaft. There may be more than one spoke, one for each of the supporting arms.

In order to move from the deployed state to the collapsed state, the ring may collapse. This may occur by having one (only) pair of adjacent segments in the ring that is not physically attached/fixed to one another (though they may of course be in contact with each other in the ring). The supporting arms may be actuated by the actuator mechanism to rotate and pivot them relative to the shaft (as described above) and to slide them relative to the shaft (as described above). The actual actuation force may directly cause (only) the rotation, the pivoting and/or the sliding. The other motion(s) may be caused indirectly as a consequence of the configuration of the anvil and supporting arms. For instance, tension may be applied (via the actuator line) to slide the supporting arms toward each other.

When the supporting arms are actuated, their motion may cause the ring to collapse. The ring may collapse such that is opens out into a generally straight line. This may occur by having each pair of physically attached adjacent segments pivot outwardly with respect to the curvature of the ring.

As the segments pivot outwardly with respect to the curvature of the ring, the anvil may change from a ring shape towards a straight-line shape. The general orientation of the anvil also may change as this occurs. The orientation may change from being perpendicular to the first direction when in the deployed state to (or towards) the first direction in the collapsed state. This orientation change may necessarily/automatically occur due to the manner in which the supporting arms are connected to the anvil and the shaft, and since the supporting arms may have fixed lengths.

The opposite motion occurs in the deploying stage (e.g. from collapsed state to deployed state).

An anvil ring that collapses in this way, in its collapsed state, may take the form of a straight line of segments. This line of segments overlaps the shaft in the first direction, e.g. it extends from a location proximate or at the distal end of the shaft, back along the shaft toward the proximal end. The line of segments may be adjacent to, e.g. as close as possible to, preferably touching, the shaft. This helps to minimise the area of the anvil in the collapsed state.

In the collapsed state, one of the supporting arms may be connected to the shaft at a location proximate to, preferably at, the distal end of the shaft. This supporting arm may not be slidable relative to the shaft. The remaining supporting arms may be connected to the shaft at locations distant from the distal end of the shaft. Each supporting arm may be located at different locations on the shaft.

In the collapsed state, each of the supporting arms may extend substantially in the first direction adjacent to (e.g. as close as possible to, such as touching) the shaft. The supporting arms may be between the anvil and the shaft.

In the collapsed state, each of the supporting arms may extend from the location at which they are attached to the shaft toward the proximal end.

There may be two, three, four or five supporting arms. Each of these may take the form of a single member, one end of which is connected to the shaft and one end of which is connected to the anvil.

In the deployed state, the members may extend in the plane of the ring in the radial direction. In the collapsed state, the members may extend parallel to the length-direction of the collapsed ring segments, i.e. substantially parallel to the first direction. In the collapsed state, the members may be located in between the collapsed anvil and the shaft.

The stapler may comprise a head portion at or toward the distal end of the stapler. The shaft and/or the anvil and/or the supporting arm(s) may be housed within the head, and may be extendable out from the head in the distal direction, or may be extendable out from the head in the distal direction.

The head may comprise a housing around the shaft and/or the anvil and/or the supporting arm(s). The housing may be a tube. The distal end of the tube may have a substantially similar shape (in both size and shape) to the deployed shape of the anvil. For instance, the distal end of the tube is preferably a circular tube (e.g. a cylinder).

The distal end of the head may comprise openings for allowing staples to pass through the head. The holes may generally form the shape of the tube. There may be a ring of openings, or a double ring of openings.

The head and the anvil may be arranged and shaped such that when the anvil is in the deployed position, and the stapling operation is carried out, body tissue is held between the anvil and the head and staples are pushed through the holes and through the body tissue held between the head and the anvil. When the staples meet the anvil, the anvil provides resistance to the staples so that the staples fold and hold the tissue. This may provide a ring of staples.

The ring of staples may be a double ring of staples (e.g. an inner ring an inner ring and an outer ring, which may be concentric, similarly shaped and closely spaced).

The head may comprise a stapling mechanism, such as those known in prior systems, i.e. that all staples are fired at once.

However, the inventors have realised that it is desirable to reduce the force required to be reacted to by the anvil. In the past, a sturdy anvil could be supplied since there was no requirement for the anvil to be flexible or to collapse into a small size (the anvil was inserted from the second side). However, due to the flexible collapsing nature of the present anvil, the inventors have identified that it may be beneficial to reduce the forces the anvil is required to react to during the stapling process.

In order to achieve this, the head may be configured such that the staples can be fired sequentially. For instance, each staple may be fired at a different time, or a first portion of the staples (such as the inner ring of staples) may be fired before or after a second portion of the staples (such as the outer ring of staples).

The head may comprise a sharp edge for cutting the body tissue. The edge may be located at the distal end of the head and at the inner side of the tube of the housing, preferably around the entire inner side of the tube. The sharp edge may therefore have the same shape as the inner of the tube. For instance, when the tube is circular, the sharp edge is circular.

The stapler may be arranged to use the sharp edge to cut away the tissue inside the ring of staples at the same time as the stapling operation or after having stapled the tissue. This forms a hole in the tissue within the stapled ring. The cut away tissue can be removed with and/or using the stapler.

The sharp edge may be arranged to press against the cutting surface mentioned above.

The sharp edge may be sloped or may not be sloped.

Alternatively, the head, the sharp edge and the anvil may be shaped such that the (radially) innermost surface of the anvil ring cooperates with the sharp edge to cut the tissue proximate the (radially) innermost surface of the anvil. The ring-shape of the anvil (i.e. the fact there is a gap/hole in toward the centre of the anvil) can thus be used advantageously during the cutting process.

This is different to the prior art systems where circular knife edge is simply pressed up through the tissue and against a planar anvil. This cuts the tissue. However, more force is required for the prior art method, and hence a more sturdy anvil is required. In the past this was not such an issue, since the anvil could be quite heavy-duty since there was no requirement for it to be flexible or collapsible. However, the inventors have identified that it may be beneficial to reduce the forces the anvil is required to react to during the stapling process, since the present anvil may be weaker due to its flexible collapsible nature.

Indeed, to further reduce the force the anvil is required to react to, the inventors have found that using a sloped sharp edge, such that the cutting occurs at different times at different locations relative to the anvil may be beneficial. The sloped sharp edge may be sloped with respect to the first direction, i.e. different locations on the sharp edge are at different positions relative to the first direction. Thus, when the sharp edge is moved in the first direction, it only cuts at one or two places simultaneously.

Alternatively, the sharp edge could comprise a sharp edge that only cuts at one location at a time, which (when in contact with the tissue) is moveable in a closed path (e.g. around the inner side of the tube of the head, or the innermost surface of the anvil. This would also cut out a portion of tissue from the inside the stapled ring whilst reducing the force required to be reacted to by the anvil.

Further, to reduce the force on the anvil, the stapler may be configured such that the cutting occurs at a different time to the stapling operation and preferably after the stapling operation.

The stapler may be configured such that when the stapler is actuated (e.g. which would happen after the collapsed anvil is positioned through a small hole in the tissue such that the tissue is in between the anvil and the stapler head), the following occur sequentially: the anvil is deployed; the anvil and the head are drawn together; when the anvil is proximate to the stapler head (i.e. adjacent to, such as pressing against (via the tissue)) the staples are fired sequentially (e.g. as discussed above); and preferably the sharp edge is actuated to cut out the tissue inside the ring of staples.

This sequential configuration reduces the amount of force on the anvil at any one time.

The small hole may be a hole that is cut in the tissue prior to insertion of the anvil through the hole. A guide, such as a (plastic) tube, may be placed through such the small hole to ease insertion of the collapsed anvil therethrough.

Preferably the actuation mechanism of the stapler is configured such that the sequential actuation occurs by the user making only one actuating action. Such an actuation action may for example be applying a force, such as a tension force, such as by squeezing a trigger or a handle. The only one actuation action may be continuous over the stapling operation (e.g. the user may be required to apply the actuation action over the entire stapling operation), or may be an instantaneous action which sets off the stapling operation.

Alternatively, the stapler may be configured such that the sequential actuation occurs by the user making several different actuating actions.

The anvil may be configured to be attachable to and detachable from the remainder of the stapler, preferably at the distal end of the stapler. The anvil may be configured to be attachable to and detachable from the shaft of the stapler. The means for actuating the anvil may be attachable to and detachable from a means for controlling the actuation located on the remainder of the stapler.

In a second aspect, the invention provides an anvil for providing resistance to staples during the stapling operation of a surgical stapler, the surgical stapler comprising a proximal end and a distal end wherein the proximal end is proximate to the user in use and the distal end is distal from the user in use: wherein the anvil is locatable at the distal end of the surgical stapler, wherein the anvil is configured to be actuated between a deployed state and a collapsed state, wherein the anvil comprises a plurality of segments arranged end-to-end, wherein the anvil is elongated in the collapsed state, the anvil being elongated generally in a first direction, wherein the area covered by the anvil is greater in the deployed state than the collapsed state when viewed along the first direction, wherein the anvil is configured such that the segments rotate about a rotation axis along a second direction perpendicular to the first direction when the anvil is actuated between the deployed and the collapsed states, and wherein the anvil is configured such that adjacent segments pivot relative to each other about a pivot axis along a third direction perpendicular to the second direction when the anvil is actuated between the deployed and collapsed states.

The anvil may be actuatable by an actuator mechanism of the stapler, the actuator mechanism being configured to actuate the anvil between the deployed and collapsed states. The actuator mechanism may be configured to be controlled from a location on the surgical stapler towards the proximal end.

The anvil may be connected to the remainder of the stapler via supporting arm(s) and/or a shaft.

There may be provided an anvil assembly. The anvil assembly may comprise the anvil discussed in any of the first or second aspects, and a shaft to which the anvil is attached. The shaft may extend in the first direction. The anvil may be attached to the shaft by one or more supporting arms. These supporting arms may be the supporting arms described in the first aspect.

In the deployed state the supporting arm(s) may be located at a distal end of the shaft. In the collapsed state the supporting arm(s) may be located at a/the distal end of the shaft. At least one of the supporting arm(s) may be located at a distance from a/the distal end of the shaft. When in the collapsed state the supporting arm(s) may be orientated substantially parallel to the first direction. When in the deployed state, the supporting arm(s) may be orientated substantially perpendicular to the first direction.

When in the collapsed state, a first portion of the anvil may overlap with the shaft in the first direction, and a second portion of the anvil may extend beyond the distal end of the shaft in the first direction. Alternatively, when in the collapsed state substantially all of the anvil may overlap with the shaft in the first direction.

At least one of the segments may comprise a cutaway portion shaped such that said segment(s) can be fit around the shaft when the anvil is in the collapsed state.

The shaft may be a first shaft. The anvil assembly may further comprise a second shaft to which the anvil is attached. The second shaft may extend generally in the first direction. The anvil may be attached to the second shaft by one or more supporting arms. These may be the first and second shafts discussed above in the first aspect relation to the actuation of the anvil.

The anvil assembly may be configured to be connectable to and detachable from a surgical stapler. A proximal end of the shaft of the anvil assembly may be connectable to and detachable from the surgical stapler, preferably the distal end of the surgical stapler. The anvil assembly may be configured to be connectable to and detachable from the shaft of the surgical stapler. The means for actuating the anvil may be attachable to and detachable from a means for controlling the actuation located on the remainder of the stapler.

The anvil assembly with two shafts for its actuation discussed above may be of particular use when the anvil assembly is configured to be connectable to and detachable from a surgical stapler. In this case, the first shaft may be connected to the stapler, and all that is required for the anvil to be actuated is for the bracket to be pushed forward or backward along the first shaft. This force causes the sliding, rotation and pivoting of the second shaft relative to the first shaft and hence causes the anvil to be actuated.

As an alternative to this two-shaft system, it may be possible to provide a tension-actuated attachable/detachable anvil assembly (such as the wire/string/cable actuation system discussed above). This actuation system may comprise a handle that connects to the actuator line. The handle may be placed over or around the shaft of the anvil assembly and/or the shaft of the stapler. The handle may be actuated by the user of the stapler from a proximal end, for example by use of another actuator line connected to the handle from the proximal end.

The anvil, the anvil assembly, the supporting arm(s), the shaft and/or the stapler may comprise any of the features discussed above in relation to the first aspect.

In a third aspect, the invention provides a method of actuating the anvil, the anvil assembly, and/or stapler of the first and/or second aspects.

The method comprises a user operating the actuator mechanism, e.g. via the handle, to actuate the anvil between the collapsed and deployed states.

The anvil may be deployed and controlled from the proximal end only. Thus, the user may not require access to the tissues to be stapled from the other side in order to deploy and control the anvil and/or stapler. In some situations however the user may well require access from the distal end to aid the deployment of the anvil (e.g. to hold the tissue during insertion of the anvil through the tissue), but even in this situation the anvil is still inserted through the tissue from the proximal end.

The method may comprise inserting the stapler into the body to a location where tissue is to be stapled.

The method may comprise making a small cut in the tissue. This may form a small hole. The hole may be made by a sharp cutting element of the stapler and/or anvil.

The cutting element may be in the form of a tip fitted onto the distal end of the anvil, when the anvil is in its collapsed state. The tip may be shaped such that it is sufficiently sharp to cut through the tissue, i.e. the tip may be sharp and/or pointed. The tip may be separate element to the anvil. The tip may be removed when the anvil is actuated into its deployed state, or prior to the anvil being actuated into its deployed state. The tip may be made of plastic. The tip may be removed manually. However, preferably, the tip may be made of a material that is dissolvable in the body. In this way, after cutting the hole, the tip may automatically dissolve.

The tip may be an elongated tube. The elongated tube may be needle-shaped (i.e. it may have a diameter significantly smaller than its length). The tube may have a substantially circular cross-section. The tube may taper towards a sharpened end, which is preferably closed. The stapler may comprise the tube. The tube may extend in the first direction. The tube may extend beyond the anvil, and/or the anvil may be located within the tube (e.g. when the anvil is in the collapsed state).

Alternatively, the cutting element may be part of the anvil itself. For instance, the anvil may be shaped such that when it is in the collapsed state the most distal end of the anvil is sufficiently sharp to cut through the tissue, i.e. the tip of the collapsed anvil may be sharp and/or pointed.

In use, the stapler may be used to staple together two pieces of tissue. These may be a proximal piece of tissue (i.e. a piece of tissue closer to the stapler) and a distal piece of tissue (i.e. a piece of tissue further from the stapler). The two pieces of tissue may be two tubes, preferably two closed ends of two closed tubes.

The cutting element may be used to cut through the proximal piece of tissue, preferably only this piece of tissue. The cutting element is moved together with the collapsed anvil (to which it is attached or part of) toward the distal direction toward the tissue. When they reach the tissue, the cutting element cuts through the proximal piece of tissue. Continued movement in the distal direction allows the cutting element and the anvil to pass through the cut hole in the proximal piece of tissue. The cutting element may then be removed, as discussed above. The collapsed anvil may then be inserted through a hole in the distal piece of tissue (which may also have been cut by the cutting element, but which is preferably cut by another means). Once inserted through this hole, the anvil can be deployed and the stapling operation can be carried out.

Alternatively, the small hole (e.g. in the proximal and/or distal piece of tissue) may already be present.

A guide, such as a (plastic) tube, may be placed through the small hole to ease insertion of the collapsed anvil therethrough.

The method may comprise passing the collapsed anvil through the small cut/hole or guide in the tissue.

The method may comprise actuating the anvil to the deployed state.

The method may comprise stapling the tissue. This may comprise bringing the stapler head toward the anvil (or vice versa), with the tissue in between the head and the anvil. The staples may be fired sequentially, as discussed above.

The method may comprise cutting the tissue within a ring of staples formed by the stapling. This may occur as the stapler head is brought toward the anvil. The cutting may be performed substantially simultaneously (though preferably just after) stapling. This may form an opening in the tissue within the stapled ring.

The method may comprise actuating the anvil to the collapsed state.

The method may comprise withdrawing the stapler from the location. The cut out piece of tissue may also be withdrawn with the stapler.

Preferably, the above method is performed in sequence, in the order set out.

In a fourth aspect, the invention provides a method of stapling a tissue using an anvil and a stapler head, wherein the following steps are performed sequentially. When the anvil is position on one side of a piece of tissue to be stapled and the stapler head is on the other side of the piece of tissue to be stapled, the method comprises: drawing the anvil and the stapler head toward together; and when the anvil is proximate to the stapler head (i.e. adjacent to, such as pressing against (via the tissue)), firing staples sequentially from the stapler head through the tissue such that the anvil offers resistance to fold the staples. Preferably, the method also comprises actuating a sharp edge of the stapler head to cut out the tissue inside a ring of staples.

This sequential configuration reduces the amount of force on the anvil at any one time.

Preferably the sequential actuation occurs by the user making only one actuating action. Such an actuation action may for example be applying a force, such as a tension force, such as by squeezing a trigger or a handle. The only one actuation action may be continuous over the stapling operation (e.g. the user may be required to apply the actuation action over the entire stapling operation), or may be an instantaneous action which sets of the stapling operation.

Alternatively, the sequential actuation may occur by the user making several different actuating actions and/or by some of the actuating steps occurring automatically. For instance, the stapling can occur by an automatic electrically-powered stapling action.

The stapler and/or anvil may be the stapler and/or anvil of the first and/or second aspects. This method may comprise any of the features of any of the other aspects.

To further reduce the force required to be reacted to by the anvil, the staples may comprise shape memory material, for example a memory metal such as nitinol. Such staples may have their original/natural shape in the folded state. The staples may be deformed such that they are held in the stapler head in the open state, and are hence fired from the stapler head in the open state. Since their original/natural state is closed, then they at least partially automatically close after having being fired, e.g. after having quickly passed through the tissue.

The properties of the shape memory material (possibly in combination with the temperature of the body) may aid the folding of the staples, and hence may reduce the required strength/rigidity of the anvil.

Alternatively, however, the staples may be stainless steel. Stainless steel is commonly used in surgery.

BRIEF DESCRIPTION OF THE DRAWINGS

Certain preferred embodiments will now be described by way of example only and with reference to the accompanying drawings, in which
FIG. 2 shows an overview of a method of stapling tissue;
FIG. 4 shows a first embodiment of an anvil.

FIG. 10 shows a sixth embodiment of an anvil;

FIG. 15 shows a tenth embodiment of an anvil as part of an anvil assembly;

DETAILED DESCRIPTION

Figure 1:
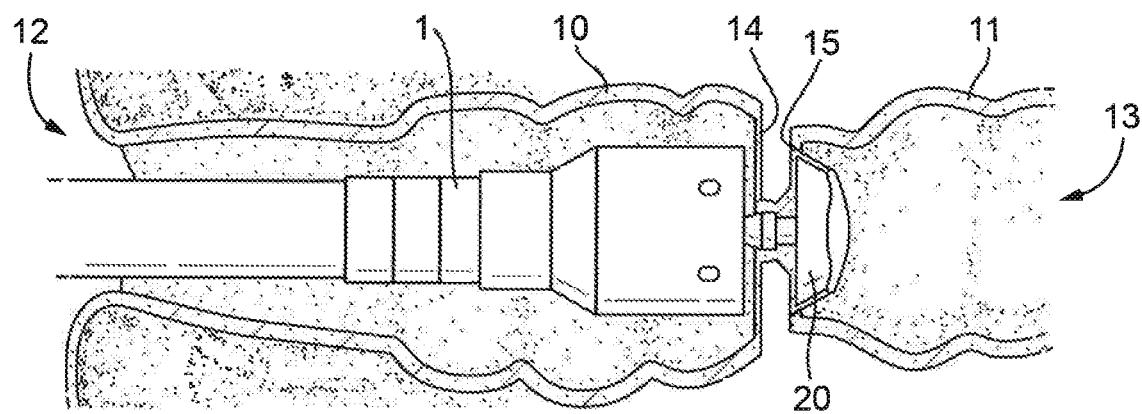
FIG. 1 shows a prior art stapler and anvil in use.

With regard to FIG. 1, the prior art stapler 1 and anvil 20 are used to connect two tubes of the body together. These tubes may be for instance two portions of the gastrointestinal tract (such as the oesophagus, stomach, duodenum, jejunum, ileum, colon and/or rectum. The two portions may have become separated when some intermediate portions of the tissue has been removed, for example when cancerous tissue is removed.

In the prior art, the stapler 1 is inserted into tube 10 from a proximal end 12. The anvil 20 is inserted into the tube 11 from the distal end 13. Thus, to staple the two tubes 10, 11 together, access is required from two sides 12, 13. The ends 14, 15 of the two tubes 10, 11 are typically sealed, for example by staples or stitches. This sealing has occurred prior to the present stapling method, for example during removal of intermediate portions of the tissue.

During stapling, the anvil 20 and the stapler 1 are pressed toward each other. This draws the ends 14, 15 of the two tubes 10, 11 towards each other. When the anvil 20 presses against stapler 1, and the tissue of the ends 14, 15 of the tubes 10, 11 are effectively clamped between the stapler 1 and the anvil 20, the stapler 1 can fire staples toward the anvil 20 and hence through said tissue. The anvil 20 provides resistance to said staples and hence aids in their folding. Once folded, the staples hold the two tubes 10, 11 together. The stapler 1 and anvil 20 are circular and produce a double concentric ring of staples.

The stapler 1 comprises a circular knife edge (not shown) that is then pressed against the anvil 20 inside the ring of staples. This cuts through the ends 14, 15 of the tubes 10, 11, thus forming a path between the tubes 10, 11. The stapler 1 is then removed from the proximal end 12 and the anvil is removed from the distal end 13.

With regard to FIG. 2, a proposed method is shown. Like the prior art method of FIG. 1, this method is for joining two tubes 110, 111 together. However, unlike the prior art, access is only required from the proximal end 112: access is not required from the distal end 113.

In FIG. 2a, a stapler 101 is introduced into the first tube 110 from the proximal end. The stapler 101 comprises a collapsible anvil 120. In FIG. 2a, the anvil 120 is in its collapsed state. In FIG. 2b, the anvil 120 is passed through the closed end 114 of the first tube 110. This is achieved by cutting through the closed end 114 with a cutting element 121 attached to the distal end of the anvil 120 when in the collapsed state. The cutting element 121 is a cutting tip 121 that can be removed manually from the anvil 120 once a hole is formed in the closed end 114, or may be made of material such that it dissolves in the body after the hole is formed. A small hole 116 is formed in the closed end 115 of the second tube 111. The small hole 116 is formed by another means (i.e. not by the stapler 101). In FIG. 2c, the anvil 120 is passed through the small hole 116. In FIG. 2d, the anvil 120 is actuated to its deployed state. More details on how this is achieved are provided below. In the deployed state, the area covered by the anvil 120 is significantly larger than the in the collapsed state.

In FIG. 2e, the anvil 120 is drawn toward the stapler head 102 such that the ends 114, 115 of the tubes 110, 111 are held between the anvil 120 and the stapler head 102. Once this occurs, staples are fired sequentially from the stapler head 102 through the two layers of tissue and are folded over by the resistance offered by the anvil 120. This joins the two tubes 110, 111 together by a double ring of staples 118. Once this occurs, a sharp edge (not shown) of the stapler head 102 cooperates with the inside of edge of a ring of the anvil 120 to cut out a portion of the ends 114, 115, thus leaving an opening 117 between the first and second tubes 110, 111. In FIG. 2f, the anvil 120 is actuated to its collapsed state and the stapler 101 can then be removed from the proximal end 112.

Figure 3:
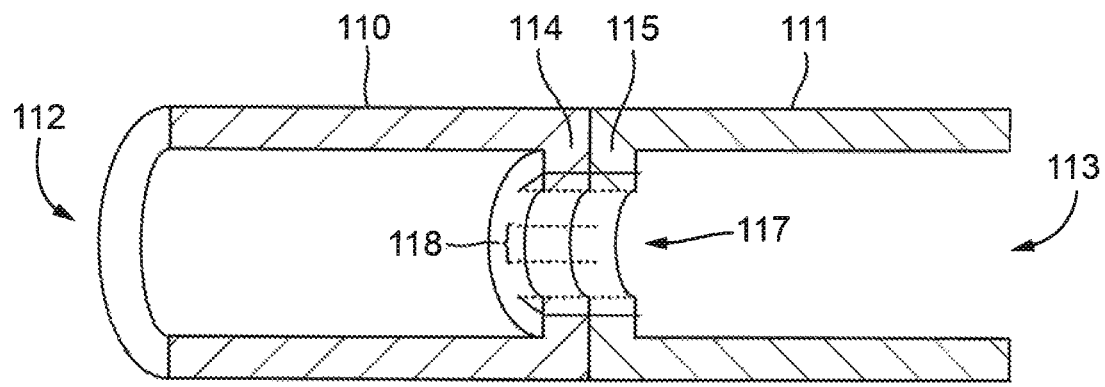
FIG. 3 shows the result of the method of FIG. 2.

With regard to FIG. 3, this shows the result of the method of FIG. 2 once the stapler 101 has been withdrawn. As can be seen, the two tubes 110, 111 are held together with a ring of staples 118 (which is preferably a double ring, though not shown). The staples 118 are folded over on the distal side of end 115, though this cannot be seen from FIG. 3. The hole 117 provides a passage through ends 114, 115 between the two tubes 110, 111.

With regard to FIG. 4, a first embodiment of the anvil 220 is shown. The anvil 220 is configured to be actuated between a deployed state (FIGS. 4b and 4c) and a collapsed state (FIG. 4a). The anvil 220 comprises a plurality of segments 230 arranged end-to-end. The anvil 220 is elongated in the collapsed state, the anvil 220 being elongated generally in a first direction ($D_1$). The area covered by the anvil 220 is greater in the deployed state ($A_D$) than the collapsed state ($A_c$) when viewed along the first direction. The anvil 220 is configured such that the segments 230 rotate about a rotation axis along a second direction ($D_2$) perpendicular to the first direction ($D_1$) when the anvil 220 is actuated between the deployed and the collapsed states. The anvil 220 is configured such that adjacent segments 230 pivot relative to each other about a pivot axis along a third direction ($D_3$) perpendicular to the second direction ($D_2$) when the anvil 220 is actuated between the deployed and collapsed states. In FIG. 4a, when the anvil 220 is collapsed, the third direction ($D_3$) is perpendicular to the first direction ($D_1$). However, as the segments 230 rotate about the second direction ($D_2$) to the deployed state, the third direction ($D_3$) also rotates. In the deployed state, the third direction ($D_3$) is parallel to the first direction ($D_1$), as can be seen in FIGS. 4b and 4c.

The anvil 220 is actuated by an actuator mechanism (not shown) of the stapler. The actuator mechanism comprises an actuator line (not visible in FIG. 4, but visible in FIG. 5) that passes through the segments 230. When tension is applied to the anvil 220 via the actuator line, the anvil 220 is actuated from the collapsed state to the deployed state. When tension is not applied (or released), the anvil 220 collapses into the collapsed state.

In the collapsed state, all adjacent segments 230 are physically attached or fixed to each other. This physical attachment may be via a hinge or pivot point, and/or at least via said actuator line.

In the deployed state, as can be seen in FIG. 4b, all but one pair of adjacent segments 230 of the anvil are physically attached or fixed to each other. There are two adjacent segments 231, 232 that are not physically attached to each other.

The actuator line is fixed to the distal-most segment 231. The actuator line is free to move relative to each of the segments 230 it passes through. However, when tension is applied, the actuator line cooperates with the distal-most segment 231 such that the tension in the actuator line pulls the distal-most segment 231 toward the other segments 230, thus acting to compress the segments 230. The segments 230 are shaped such that when this tensioning occurs, the anvil 220 changes from its collapsed to its deployed state.

During actuation, each segment 230 rotates and pivots. All of the segments 230 of the anvil rotate the same amount, which is about 90°.

Each segment 230 has a length (L), which is generally oriented in the elongated direction of the anvil in the collapsed state ($D_1$), and is orientated generally perpendicular to the first direction ($D_1$) when in the deployed state. Each segment 230 is generally elongated (even if it is curved) and the length (L) is generally in the direction of said elongation.

Each segment 230 has a width (W). The width (W) is perpendicular to the length (L). The width (W) of each segment 230 defines the surface for providing resistance to the staples during the stapling operation. The width (W) should therefore be sufficiently large to provide a large enough area to provide resistance to the staples during the stapling operation.

Each segment 230 has a depth (d). The depth (d) is generally perpendicular to the length (L) and the width (W). The depth (d) should be sufficient for providing adequate strength and rigidity to the anvil 220 for providing resistance during the stapling operation. The depth (d) direction may be orientated generally in the first direction when the anvil is deployed.

Each segment 230 may comprise two ends 233, 234, one at each end of the length (L) of the segment, and extending across the width (W) and depth (d) of each segment 230.

These ends 233, 234 comprise respective end surfaces.

The segments 230 are shaped such that when the anvil 220 is in its deployed state, the segments form a rigid anvil 220. The segments may be shaped such that when the anvil 220 is in its deployed state, the end surfaces 233, 234 of the adjacent segments 230 abut each other. This abutment is such that there is greater end surface 233, 234 contact between adjacent segments 230 when the anvil 220 is deployed than when the anvil 220 is collapsed. Further, as mentioned above, there is a compression force present that forces the segments 230 in a way that increases the contact and/or friction between the end surfaces 233, 234 of adjacent segments 230, but does not cause any movement of the segments 230 due to their shape—the segments 230 are shaped to provide a reaction force. Thus, the segments 230 are stressed when in the deployed state, and are held against movement (despite the force being present) by the shape of each segment 230 causing an interaction between the end surfaces 233, 234 of neighbouring segments 230, which provides the reaction force and hence maintains the stressed state.

As shown in FIG. 4, each of the segments 230 is curved. These curves are arc-shapes. The arc-shape is an arc of a circle. The segments 230 are curved such that they collectively form a substantially continuous circle shape when the anvil is deployed (as can be seen in FIG. 4b).

Both the outermost periphery of the segments 230 when in the deployed state and the innermost periphery of the segments 230 when in the deployed state define circular shapes, which are concentric.

The ends of the segments 233, 234 are perpendicular to the direction of the curve (e.g. the tangent of the circle) of the segment 230 at the respective ends 233, 234 of the segment 230. The ends 233, 234 extend in the radial direction of the circle, when deployed.

Adjacent segments 230 pivot relative to each other about a pivot point 235. The pivot point 235 is located where the end of one segment 233, 234 meets the end of an adjacent segment 230, when the anvil 220 is in the collapsed state.

In the deployed state, the anvil 230 is a ring-shape. The ring is substantially continuous. By substantially continuous, it is meant that the ring is at least largely complete, but there is a minor break minor break in the ring. For example, a distal end of the end segment 231 of the anvil is not physically attached to its adjacent segment 232 when in the deployed ring shape. However, it may be pressed against said adjacent segment 232 by compression forces. The ring is a circular shape.

All of the segments 230 of the anvil 220 are orientated such that they extend (e.g. the direction from one end 233 of a segment to the other end 234 of the same segment, i.e. the length direction (L)) substantially perpendicular to the first direction ($D_1$) when the anvil 234 is deployed.

When the anvil 220 is deployed, the segments 230 of the anvil 220 define a plane. The normal of this plane is substantially parallel with the first direction ($D_1$).

The area covered by the anvil ($A_D$) is the area defined by the outer periphery of the anvil ring 220 when in the deployed state. Of course, the actual area provided by the anvil for providing resistance to staples may be smaller than the area covered by the anvil, since not all of the area covered by anvil may provide resistance to staples since there may be gaps (e.g. the area of an annulus is smaller than the area of a circle). The actual area provided by the anvil is determined by the circumference of the wring and the width (W) of the segments 230.

The rotation of the segments 230 about a rotation axis in the second direction ($D_2$) may be thought of as a re-orientation of the segments 230 between the collapsed and deployed states. The rotation is of the general length-direction (L) of the segments 230. For instance, in the collapsed state, the length-direction (L) of the segments is generally in the first direction ($D_1$). However, during deployment this length-direction (L) rotates about an axis in the second direction ($D_2$). Thus, in the deployed state, the length-direction ($D_2$) of the segments is not in the first direction ($D_1$). Rather, the length-direction (L) is 90° to the first direction ($D_1$).

Each of the segments 230 rotates by substantially the same amount between the collapsed and the deployed states.

The pivoting of the segments 230 about a pivot axis in the third direction ($D_3$) may be thought of as a re-orientation of the segments 230 between the collapsed and deployed states. The pivoting may be of the general length-direction (L) of the segments. For instance, in the collapsed state, the length-directions of the segments (L) are generally in the first direction ($D_1$), and hence generally parallel and colinear with each other. However, during deployment this length-direction (L) rotates about an axis in the third direction ($D_3$). Thus, in the deployed state, the length-directions (L) of respective segments 230 are not parallel with each other. Rather, they pivot and are non-parallel with each other.

In the collapsed state, the length-directions (L) of respective segments are substantially 0° to each other. However, in the deployed state, the length-directions (L) of the adjacent segments are around 60° to each other.

Each of the segments 230 pivot relative to their adjacent segments by substantially the same amount between the collapsed and the deployed states.

When in the deployed state, the anvil 220 has a direction of curvature (C). The direction of curvature (C) is towards the centre of the circle defined by the ring anvil 220. In FIG. 4, all adjacent segments 230 pivot relative to each other in an outward direction relative to the direction of curvature (C) when the anvil 220 changes from the deployed state to the collapsed state. Such pivoting effectively straightens the ring. Correspondingly, all adjacent segments 230 pivot relative to each other in an inward direction relative to the direction of curvature (C) when the anvil changes from the collapsed state to the deployed state. Such pivoting effectively closes the ring.

Whilst the location of the axis of the pivot is different for each adjacent pair of segments (the axis of the pivot will be located at the pivot point 235 located where two adjacent segments 230 meet), every pivot axis is in the same direction as each other (the third direction ($D_3$)).

At or toward the proximal end of the stapler, the stapler may comprise a user interface, such as a handle. The user interface may be connected to the actuator and may allow the user to control the actuator mechanism.

The anvil 220 may be connected to the remainder of the stapler 101, such as the stapler head 102, via a shaft 250. The shaft 250 is elongated. The shaft 250 is located at the distal end of the stapler 101, or may be attached to the distal end of the stapler 101. The actuator mechanism (such as the actuator line) passes through the shaft 250. The shaft 250 extends generally in the first direction ($D_1$). The shaft 250 is typically located a central longitudinal axis of the stapler 101 or stapler head 102. The shaft 250 is substantially rigid and inflexible, i.e. it does not rotate or pivot like or with the anvil segments 230; rather, it may remain stationary relative to the remainder of the stapler 101 during actuation of the anvil 220.

The anvil 220 is attached to the distal end of the shaft 250. Together, the shaft 250 and the anvil 220 may form an integral anvil assembly that is attachable to or detachable from the remainder of the stapler 101. The anvil 220 is attached to the shaft 250 by a supporting arm 260. The supporting arm 260 is arranged such that the shaft 250 is within the area covered by the ring ($A_D$) when viewed along the first direction ($D_1$) when the ring is deployed. The shaft 250 is toward the centre (but not at the exact centre) of the ring.

In the deployed state, the supporting arm 260 extends partially in the plane defined by the anvil ring 220. In the collapsed state, the supporting arm extends in the first direction ($D_1$) colinearly with the collapsed anvil 220.

The supporting arm 260 comprises segments 261, similar to those of the anvil 220. The segments 261 of the supporting arm 260 are shaped such than when the anvil is actuated, the supporting arm 260 is also actuated by the actuator mechanism such that the supporting arm 260 acts to position the anvil 220 in the correct position and orientation.

The anvil 220 is attached to the shaft 250 by only one supporting arm 260.

In the collapsed state, the shaft 250, the support arm 260 and the anvil 220 may all extend substantially in the first direction ($D_1$), co-linearly in an end-to-end fashion. However, in the deployed state, the support arm 260 may act as a spoke between the deployed anvil 220 and the shaft 250.

Figure 5A:
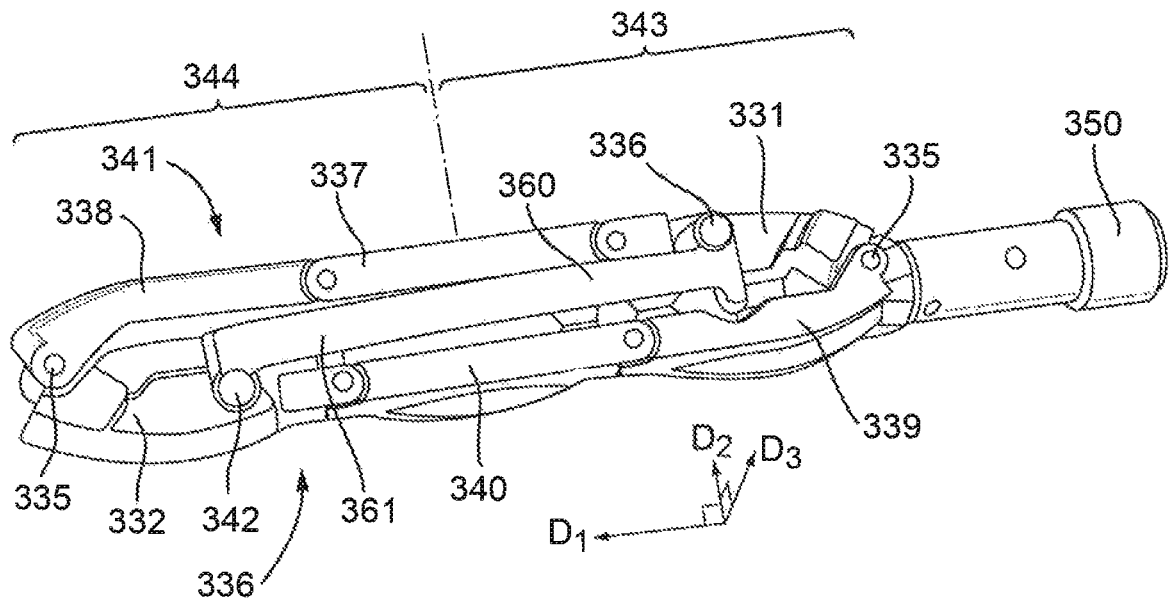
FIG. 5 shows a second embodiment of an anvil.
Figure 5B:
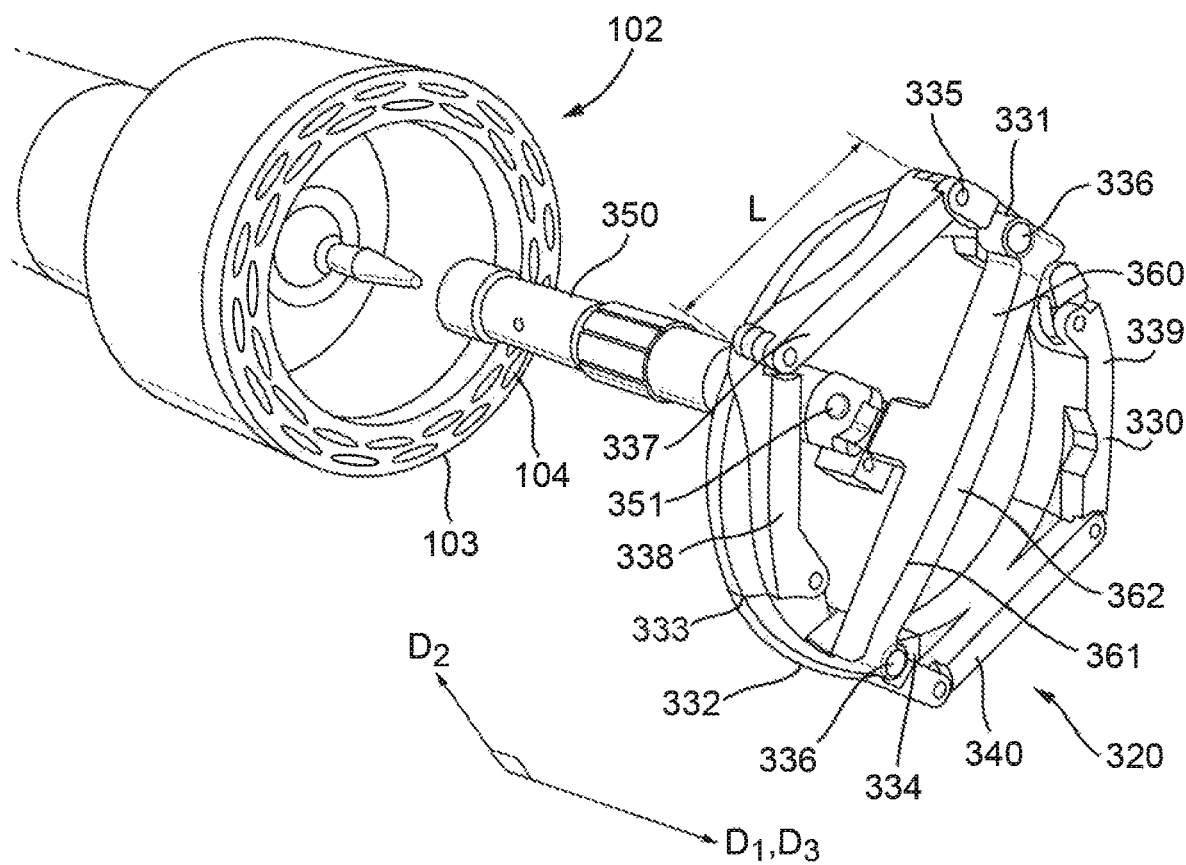

With regard to FIG. 5, a second embodiment of an anvil 320 is shown. Except where discussed below, this embodiment is substantially identical to that of FIG. 4. FIG. 5a shows the anvil 320 in the collapsed state, and FIG. 5b shows the anvil 320 in the deployed state.

The pivots 335 between adjacent segments 330 are hinges. Every segment 330 in the deployed state is physically attached to both of its adjacent segments 330.

The anvil 320 is attached to the shaft 350 by a plurality of supporting arms 360, 361. In this case there are two supporting arms 360, 361. The supporting arms 360, 361 support opposite sides of the anvil ring when the anvil 320 is deployed. The two supporting arms 360, 361 are spaced around the ring by around 180° from each other. The supporting arms 360, 361 are rotationally symmetrically arranged around the ring.

Each supporting arm 360, 361 is the same length. Thus, the shaft 350 is at the centre of the ring.

Each supporting arm 360, 361 extends between the shaft 350 and a respective segment of the ring 331, 332. The supporting arms 360, 361 attach to the respective segments 331, 332 at a point on the segment 331, 332 that is distant from either end 333, 334 of said segment 331, 332. In this case, the point is at the midpoint along the length-direction (L) of the segment 331, 332. In addition to the pivots 335 between adjacent segments 330, a pivot 336 is provided to connect the supporting arm 360, 361 to the segment 331, 332, to allow the segment 331, 332 to pivot relative to the supporting arm 360, 361 during actuation of the anvil.

Each supporting arm 360, 361 has the same length.

Each supporting arm 360, 361 pivots relative to the segments 331, 332 of the anvil about axes that are orientated in the third direction ($D_3$).

In the collapsed state, the shaft 350, the support arms 360, 361 and the anvil 320 may all extend substantially in the first direction ($D_1$), however the anvil 320 and the supporting arms 360, 361 are parallel to, but radially offset from, the shaft 350. The radial offset is as small as possible, such as the supporting arms 360, 361 and the anvil 320 are touching the shaft 350. Thus, the anvil 320 and supporting arms 360, 361 are gathered alongside the shaft 350 (i.e. they may overlap with the shaft 350 in the first direction ($D_1$)).

Adjacent segments 337, 338; 337, 331; 339, 340; 340, 332 pivot relative to each other in an outward direction relative to the direction of curvature of the anvil 320 when the anvil changes from the deployed state to the collapsed state. Thus, these adjacent segments 337, 338; 337, 331; 339, 340; 340, 332 pivot relative to each other in an inward direction relative to the direction of curvature when the anvil 320 changes from the collapsed state to the deployed state. In this case, since there are six segments, these adjacent segments 337, 338; 337, 331; 339, 340; 340, 332 pivot relative to each other by 60°.

In addition to this, adjacent segments 331, 339; 332, 338 pivot relative to each other in an inward direction relative to the direction of curvature when the anvil 320 changes from the deployed state to the collapsed state. Thus, these adjacent segments 331, 339; 332, 338 pivot relative to each other in an outward direction relative to the direction of curvature when the anvil 320 changes from the collapsed state to the deployed state. In this case, since there are six segments, these adjacent segments 331, 339; 332, 338 pivot relative to each other by 120°.

There are only two pairs of adjacent segments 331, 339; 332, 338 that pivot inwardly during collapse in this manner. The remaining segments may pivot outwardly during collapse.

When the ring collapses in such a manner, the anvil may collapse into two collapsed ring halves 341, 342, as discussed below.

In the collapsed state, a first portion 343 of the anvil and the supporting arms overlaps with the shaft 350 in the first direction ($D_1$), and a second portion 344 of the anvil 320 and the supporting arms extends beyond the distal end of the shaft 350 in the first direction ($D_1$). The first portion 343 may be called an overlapping portion 343 and the second portion 344 may be an extending portion 344. The anvil 320 and the supporting arms 360, 361 consist of the first and second portions. The first and second portions 343, 344 are generally symmetric halves of the anvil 320 and supporting arms 360, 361.

In the deployed state, the supporting arms 360, 361 may each connect to the distal end of the shaft 350. In the collapsed state, the supporting arms 360, 361 also each connect to the distal end of the shaft 350 (e.g. at the same location as in the deployed state).

This connection location may comprise a pivot 351. The axis of this pivot 351 is in the second direction ($D_2$). The anvil 320 and supporting arms 360, 361 can therefore rotate about this pivot 351 so as to rotate the segments 330 of the anvil 320 around the axis in the second direction ($D_2$). The pivot 351 is located at the distal end of the shaft 350.

In the deployed state, the anvil 320 forms a ring and the supporting arms 360, 361 form spokes connecting the ring to the shaft 350.

In order to move from the deployed state to the collapsed state, the ring may collapse. This may occur by allowing two pairs of adjacent segments 332, 338; 331, 339 to pivot inwardly with respect to each other (as is described above) and allowing the remaining pairs of adjacent segments 337, 338; 337, 331; 339, 340; 340, 332 to pivot outwardly with respect to each other. The opposite pivoting occurs in the deploying stage (e.g. from collapsed state to deployed state).

The two pairs whose segments pivot inwardly with respect to each other 332, 338; 331, 339 are substantially 180° opposite each other on the ring. The anvil 320 has an even number of segments 330.

Such a collapsed ring means that half of the segments 338, 337, 331 of the anvil form a first collapsed half 341 and the remaining segments 332, 340, 339 of the anvil form a second collapsed half 342 of the ring. These two collapsed halves 341, 342 may overlap in the first direction ($D_1$) in the collapsed state. One of the pivots 335 about which adjacent segments 332, 338; 331, 339 pivot inwards during collapse may be located at the distal end of the collapsed anvil (which is elongated in the first direction ($D_1$)) and the other of the pivots 335 about which adjacent segments 332, 338; 331, 339 pivot inwards during collapse may be located at the proximal end of the collapsed anvil.

The two supporting arms 360, 361 take the form of a single bar 362 whose midpoint is connected to the distal end of the shaft 350, i.e. at the pivot 351. This single bar 362 thus comprises both supporting arms 360, 361. The bar 362 is also connected to opposite segment 331, 332 by the pivots 336.

In the deployed state, the bar 362 extends in the plane of the ring in the radial direction. In the collapsed state, the bar 362 extends substantially parallel to the length-direction collapsed ring segments (L), i.e. substantially parallel to the first direction ($D_1$). In the collapsed state, the bar 362 is located in between the two collapsed half rings 341, 342.

The bar 362 is straight.

Although not shown, to actuate the pivoting of each supporting arm relative to the segments, an actuator line may connect between the supporting arm and the segments. The actuator line may be arranged such that when it is tensioned (e.g. by action from the user at the proximal end of the stapler), the supporting arm may pivot relative to the segments. This in turn may cause the adjacent segments to pivot relative to each other. This (possibly in combination with a suitable biasing) may drive the anvil between the deployed and collapsed states.

Both when deployed and collapsed, the anvil 320 is only connected to the distal end of the shaft 350. FIG. 5a shows the anvil 320 and the shaft 350 as an anvil assembly that is detachable from the remainder of the stapler 102.

Although not shown in FIG. 5, there may be a cutting element 121 present (shown in FIG. 2). The cutting element 121 may be in the form of a tip fitted onto the distal end of the anvil 320, when the anvil 320 is in its collapsed state (e.g. proximate to pivot 335). The tip 121 may be shaped such that it is sufficiently sharp to cut through the tissue, i.e. the tip 121 may be sharp and/or pointed. Alternatively, the anvil 320 may be placed inside a tube (see FIG. 14) to cut the tissue, or indeed the distal end of the anvil 320 when in the deployed state (e.g. proximate to pivot 335) may be shaped to form a cutting element.

Figure 6:
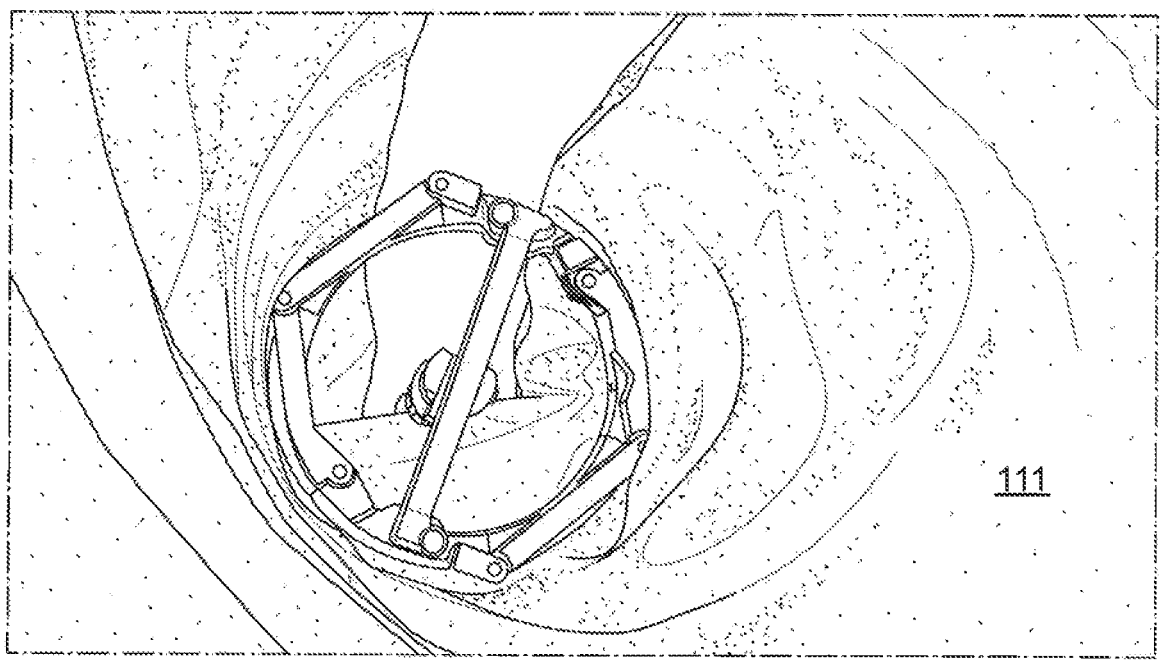
FIG. 6 shows the second embodiment in use.

With regard to FIG. 6, this shows the anvil of FIG. 5 in use inside a tube 111 of the body. As can be seen, the ring shape is sized and shaped so as to best fit into the tube without overly stretching the tube 111.

Figure 7A:
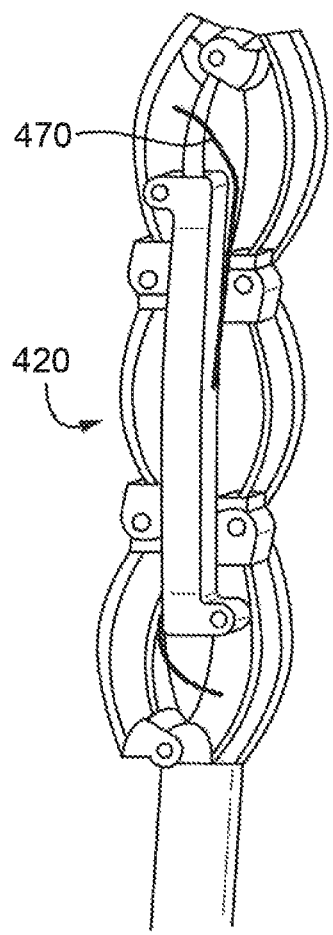
FIG. 7 shows a third embodiment of the an anvil.
Figure 7B:
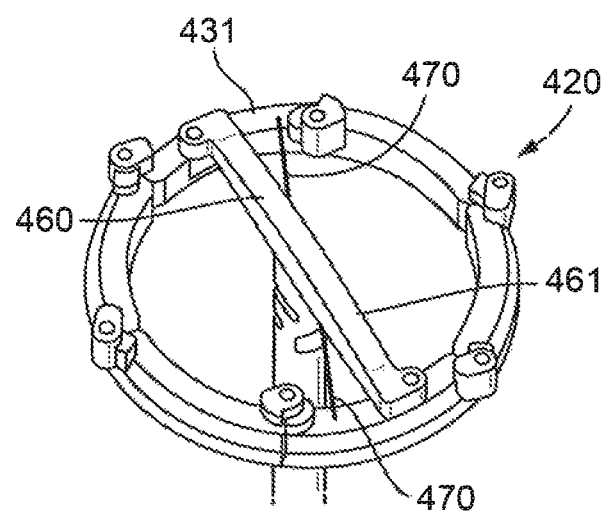
Figure 7C:
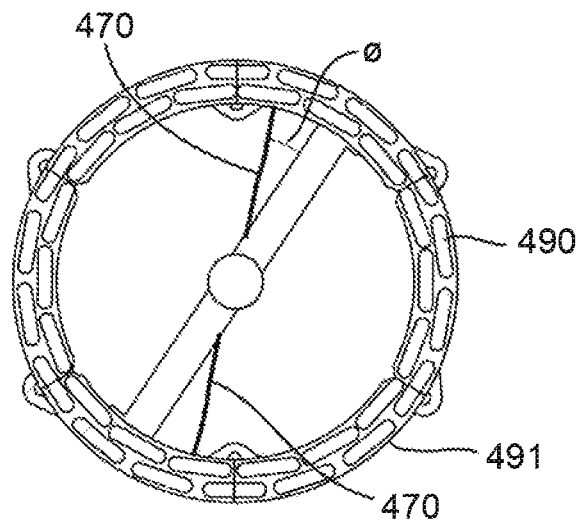

With regard to FIG. 7, a third embodiment of an anvil 420 is shown which is very similar to the second embodiment of the anvil 320. FIG. 7a shows the anvil 420 in the collapsed state, and FIGS. 7b and 7c show the anvil 420 in the deployed state.

In contrast to FIG. 5, the actuator line 470 for actuating the anvil 420 is explicitly shown. The actuator line 470 connects between the supporting arm and the anvil. A first actuator line 470 extends between the first supporting arm 460 and the segment 431 to which said supporting arm is attached. A second actuator line 470 extends between the second supporting arm 461 and the segment 470 to which said supporting arm 461 is attached. The actuator line 470 extends between the supporting arm and the anvil at an angle (θ) relative to the supporting arm. This means that when the actuator line 470 is tensioned, the supporting arm is pivoted relative to the anvil, and hence the anvil 420 can collapse.

The surface of the anvil 420 that faces the proximal end 112 when deployed may be thought of as the stapling surface 491. The stapling surface 491 is the surface that contacts the tissue and provides resistance to the staples piercing through the tissue during the stapling operation. The stapling surface 491 is generally annular.

The stapling surface 491 comprises a plurality of recesses 490. The recesses 490 are shaped and positioned so as to interact with the staples piercing through the tissue so as to assist with the folding of the staples. There may be one recess 491 per stapler head hole 104, and each recess 491 may be located to interact with a staple coming from a respective hole 104. In the specific embodiment of FIG. 7, the recesses 490 are arranged in a ring, corresponding to the ring shape of the deployed anvil 420. The recesses 490 are arranged in two concentric rings, corresponding to the two concentric rings of the openings 104 of the stapler head 102. Although only shown in FIG. 7, these recesses 490 may be present in all embodiments.

Figure 8A:
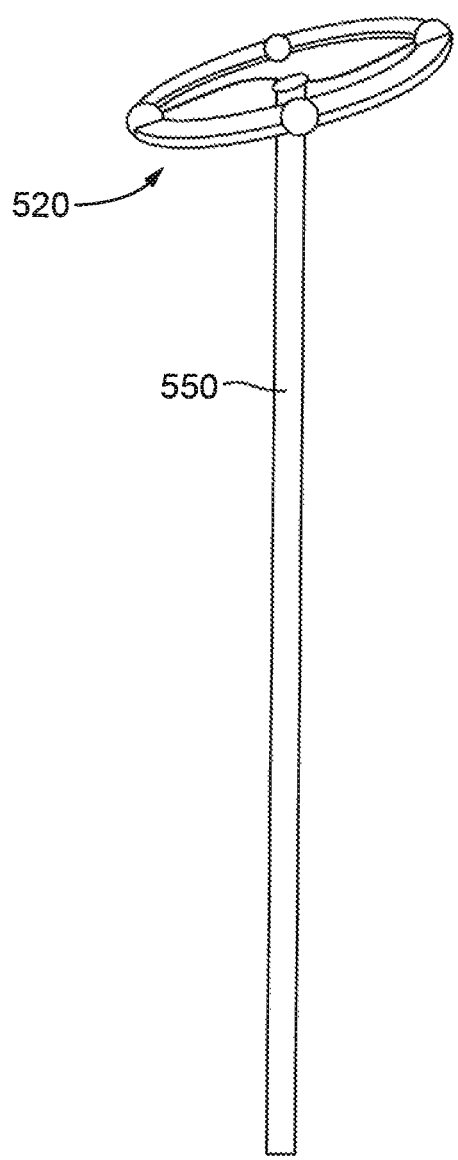
FIG. 8 shows a fourth embodiment of an anvil.
Figure 8B:
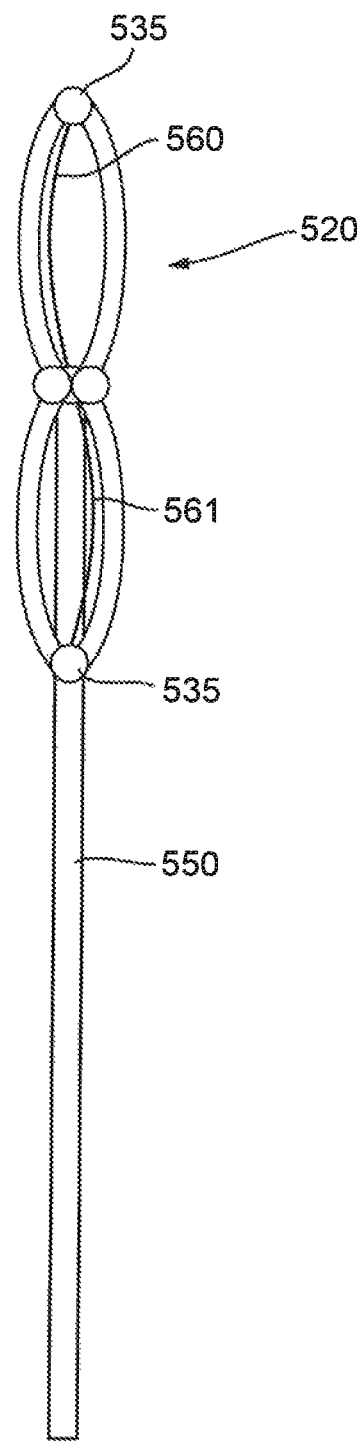

With regard to FIG. 8, this shows a fourth embodiment of an anvil 520 which is very similar to that of the second and third embodiments. FIG. 8a shows the anvil 520 in the deployed state, and FIG. 8b shows the anvil 320 in the collapsed state.

In this embodiment each supporting arm 560, 561 extend between the shaft 550 and the location 535 between adjacent segments 530 of the ring. This allows for the possibility of using the same pivot point 535 for allowing the anvil 520 to pivot relative to the supporting arm 560, 561 as is used for allowing adjacent segments 530 to pivot relative to each other. However, it does mean that the length of the supporting arm 560, 561 may need to be longer in the collapsed state than in the deployed state (or vice versa). Thus, a curved and flexible supporting arm 560, 561 can be used. Such a supporting arm 560, 561 may be inflexible/rigid in the third direction ($D_3$) but may be flexible perpendicular to the third direction ($D_3$).

Figure 9:
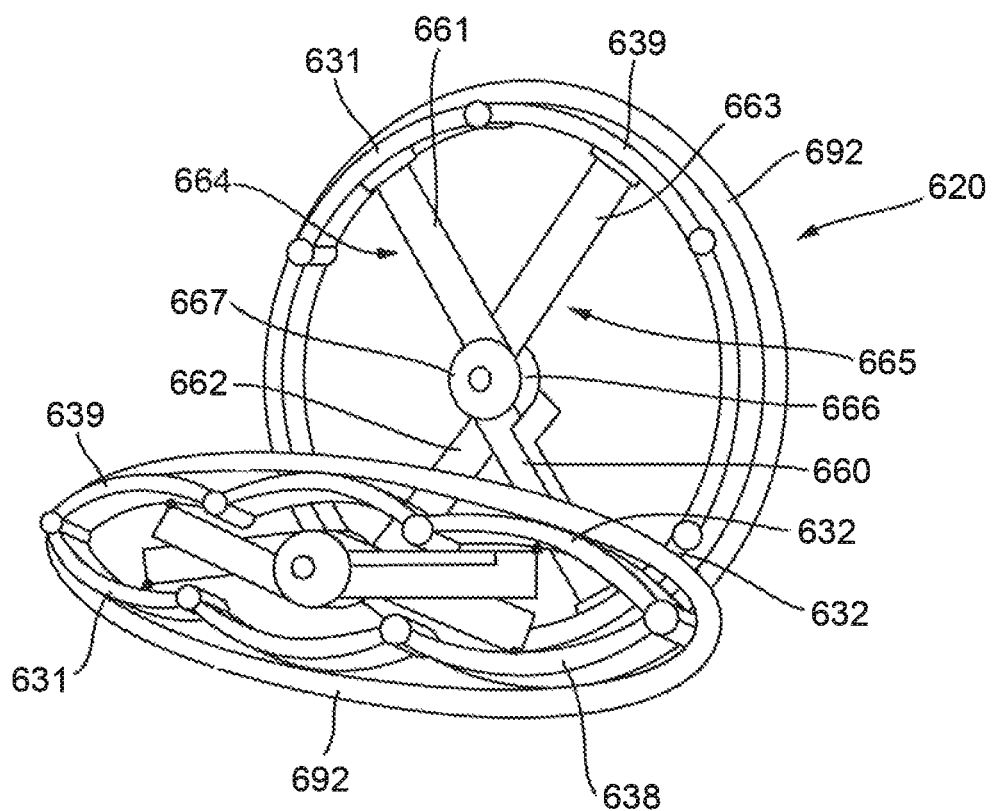
FIG. 9 shows a fifth embodiment of an anvil.

With regard to FIG. 9, this shows a fifth embodiment of an anvil 620 which is very similar to that of the second and third embodiments. However, in this embodiment, there are four supporting arms 660, 661, 662, 663. These take the form of two bars 664, 665 whose approximate midpoints are connected to the distal end of the shaft, e.g. at the pivot 351. The bar 664 comprises the two supporting arms 660, 661 and the bar 665 comprises the two supporting arms 662, 663. Each bar 664, 665 connects to two different opposite segments: bar 664 connects between segments 631 and 632 and bar 665 connects between segments 639 and 638. Each bar is connected to the respective segments in the same way as the bar of FIG. 5.

Each bar 664, 665 comprises a kink 666, 667. The kink 666, 667 is present at the location where the bar is connected to the shaft. Two straight portions 660, 661; 662, 663 of equal length join at the kink 666, 667.

When deployed, the bars 664, 665 are spaced by an angle, such as around 60°. During collapse, this angle is reduced to close to 0° such as less than 10°. The bars 664, 665 thus pivot relative to each other during collapse. This pivot is about an axis in the third direction.

The anvil 620 also comprises an outer protective ring 692. The outer ring 692 is located on the outer edge of the anvil ring. The outer ring 692 is flexible and/or elastic, and may be made from rubber. The outer ring 692 is for protecting the tissue from being caught in the moving parts of the anvil 620, which may otherwise occur during deployment or collapse of the anvil 692, or at another time.

With regard to FIG. 10, this shows a sixth embodiment of an anvil 720 which is similar to that of the preceding embodiments, except where discussed below.

In the collapsed state, all of the anvil 720 may overlap with the shaft in the first direction ($D_1$). This is shown in FIG. 10b.

In the deployed state, the supporting arms 760, 761, 762 all connect to the distal end of the shaft 750. In the collapsed state, the supporting arms 760, 761, 762 also all connect to the shaft 750, but may connect to different locations on the shaft 750.

At least two and preferably all of the supporting arms 760, 761, 762 are able to rotate about the shaft 750 (e.g. about an axis in the first direction ($D_1$)). During actuation of the anvil 720 the at least two, and preferably each, of the supporting arms 760, 761, 762 rotate about the shaft 750 (e.g. about an axis in the first direction ($D_1$)).

All of the supporting arms 760, 761, 762 are able to pivot relative to the shaft 750 (e.g. about an axis perpendicular to the first direction and perpendicular to the direction in which the respective supporting arm extends). During actuation of the anvil 720, each of the supporting arms 760, 761, 762 pivot relative to the shaft 750 (e.g. about an axis perpendicular to the first direction and perpendicular to the direction in which the respective supporting arm extends).

Two of the supporting arms 761, 762 are slidable relative to the shaft 750 in the first direction ($D_1$). During actuation of the anvil 720, the two supporting arms 761, 762 slide relative to the shaft 750 (e.g. about an axis in the first direction ($D_1$)).

Each of the supporting arms 760, 761, 762 is able to pivot relative to the anvil 720.

Each supporting arm 760, 761, 762 connects between a respective location on the anvil 720 and a respective location on the shaft 750. Each supporting arm 760, 761, 762 are connected to a different location on the anvil 720 (such as different segments 730). In the collapsed state, each supporting arm 760, 761, 762 connect to the shaft 750 at different positions in the first direction ($D_1$). In the deployed state, each supporting arm 760, 761, 762 connects to the shaft at substantially the same position in the first direction ($D_1$), e.g. at the distal end of the shaft 750.

In the deployed state, the anvil 720 forms a ring and the supporting arms 760, 761, 762 form spokes connecting the ring to the shaft 750.

In order to move from the deployed state to the collapsed state, the ring may collapse. This may occur by having only one pair of adjacent segments 731, 732 in the ring that is not physically attached/fixed to one another (though they are in contact with each other in the ring). The supporting arms 760, 761 are actuated by the actuator mechanism to rotate and pivot them relative to the shaft 750 and to slide them relative to the shaft 750.

An actuator line 770 connects each of the supporting arms 760, 761, 762. When tension is applied to the actuator line 770, the supporting arms 760, 761, 762 are drawn together thus causing the actuation toward the deployed state (i.e. from FIGS. 10a, to 10b, to 10c).

When the supporting arms 760, 761, 762 are actuated in the reverse direction (e.g. by releasing the tension and using natural resilience of the anvil 720), their motion may cause the ring to collapse. The ring may collapse such that is opens out into a generally straight line (see FIGS. 10c and 10b). This may occur by having each pair of physically attached adjacent segments 730 pivot outwardly with respect to the curvature of the ring. As the segments 730 pivot outwardly with respect to the curvature of the ring, the anvil 720 changes from a ring shape towards a straight-line shape. The general orientation of the anvil 720 also changes as this occurs, as can be seen in FIG. 10c. The orientation changes from being perpendicular to the first direction ($D_1$) when in the deployed state to the first direction ($D_1$) in the collapsed state. This orientation change necessarily/automatically occurs due to the manner in which the supporting arms 760, 761, 762 connect to the anvil 720 and the shaft 750, and since the supporting arms 760, 761, 762 have fixed lengths.

The opposite motion occurs in the deploying stage (e.g. from collapsed state to deployed state).

As can be seen in FIG. 10b, an anvil ring that collapses in this way, in its collapsed state, takes the form of a straight line of segments 730. This line of segments 730 overlaps the shaft 750 in the first direction ($D_1$). The line of segments 730 is adjacent to the shaft. Indeed, as can be seen from the plan view of FIGS. 11b and 11c, the segments 730 may comprise cutaway portions 735 so that they can more closely fit to the shaft 750 and so that the area ($A_c$) of the collapsed anvil 720 is reduced.

In the collapsed state, one of the supporting arms 760 is connected to the shaft 750 at a location at the distal end of the shaft 750. This supporting arm 760 is not slidable relative to the shaft. The remaining supporting arms 761, 762 are connected to the shaft at locations distant from the distal end of the shaft 750.

In the collapsed state, each of the supporting arms 760, 761, 762 extend substantially in the first direction ($D_1$) toward the proximal end adjacent to the shaft 750. The supporting arms 760, 761, 762 are between the anvil 720 and the shaft 750.

FIG. 10a shows a casing 780 in which the shaft 750, the anvil 720 and the supporting arms 760, 761, 762 can be held, for example during insertion through the small hole 116 in the tissue. The casing 780 is cylindrical and is part of the stapler 101.

Figure 11A:
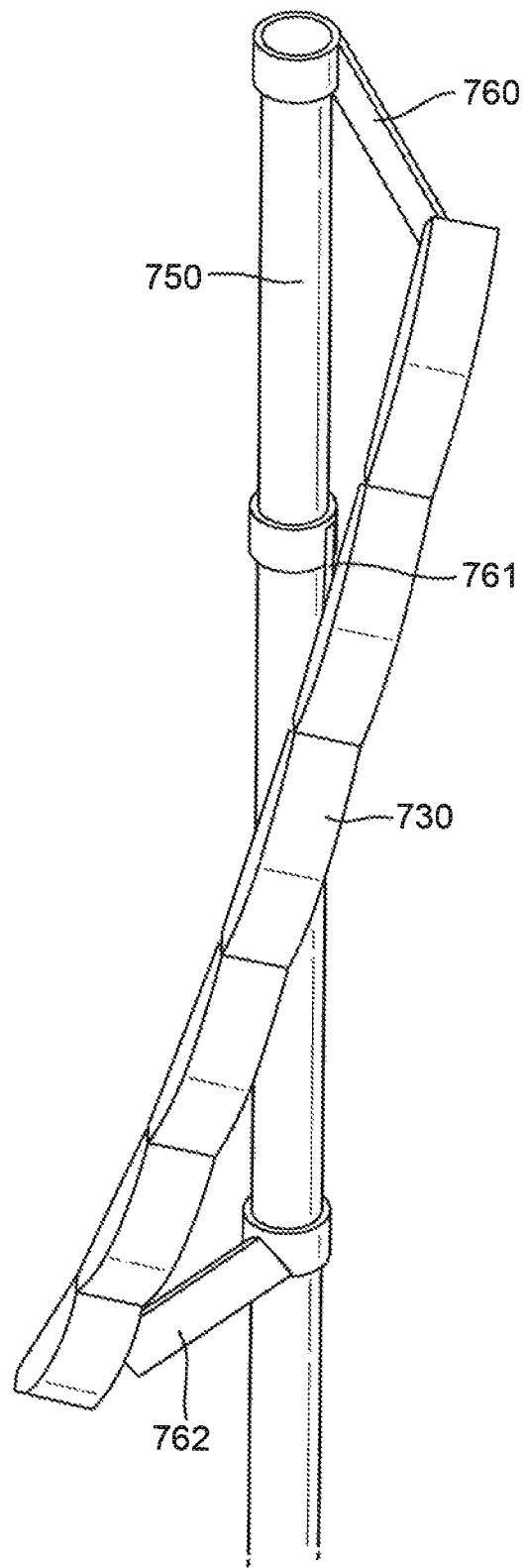
FIG. 11 shows enlarged views of the anvil of the sixth embodiment.
Figure 11B:
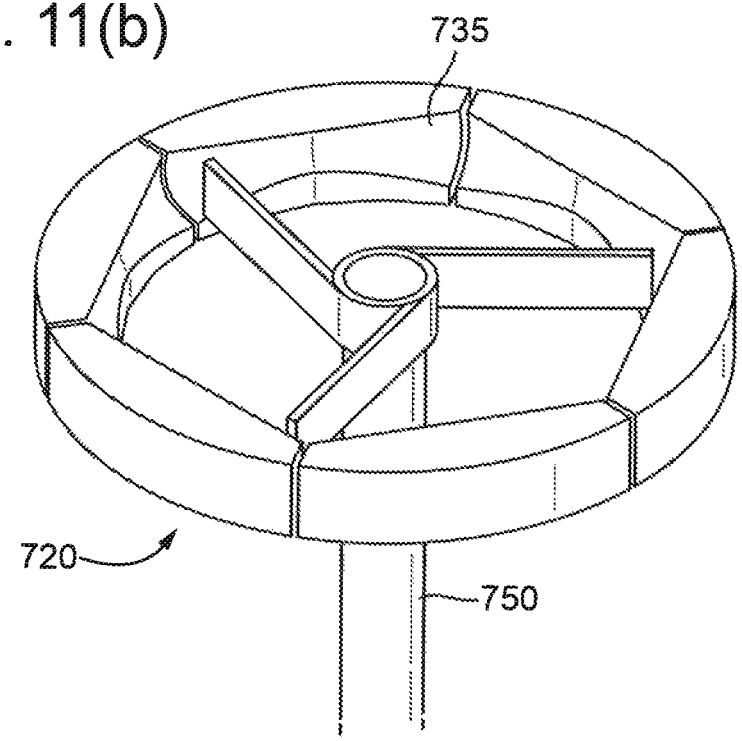
Figure 11C:
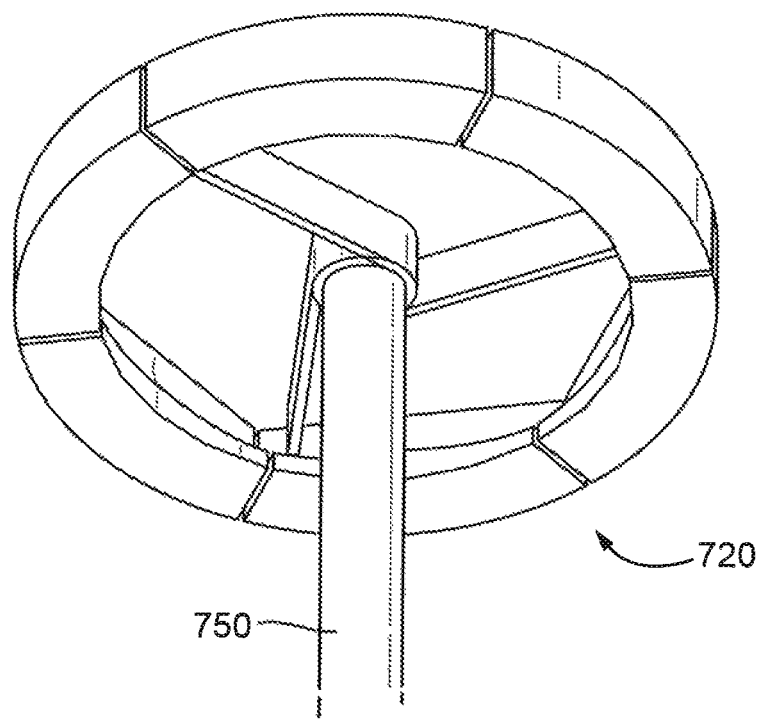

FIG. 11 shows an enlarged view of the anvil 720 of FIG. 10.

Figure 12:
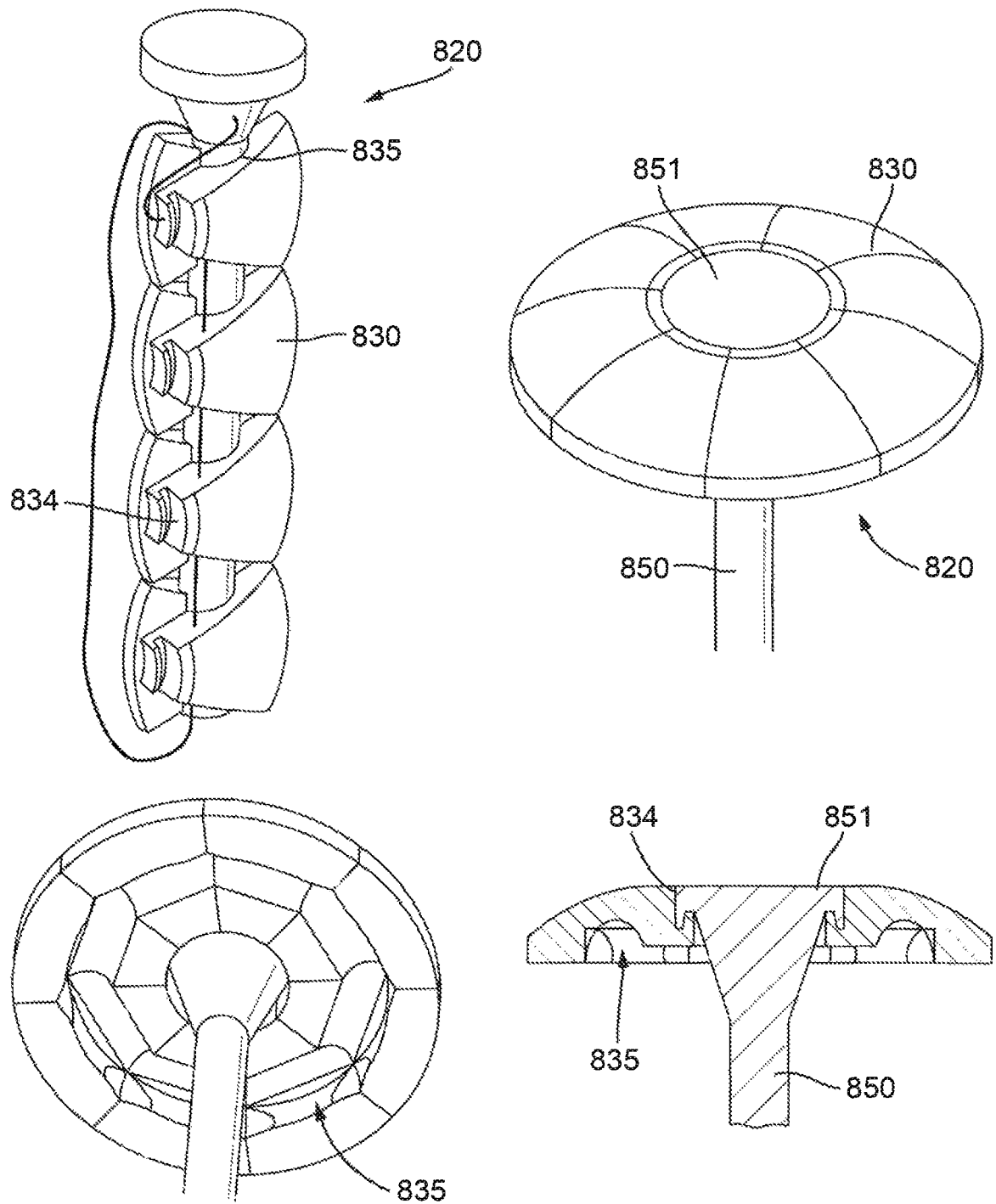
FIG. 12 shows a seventh embodiment of an anvil.
Figure 13A:
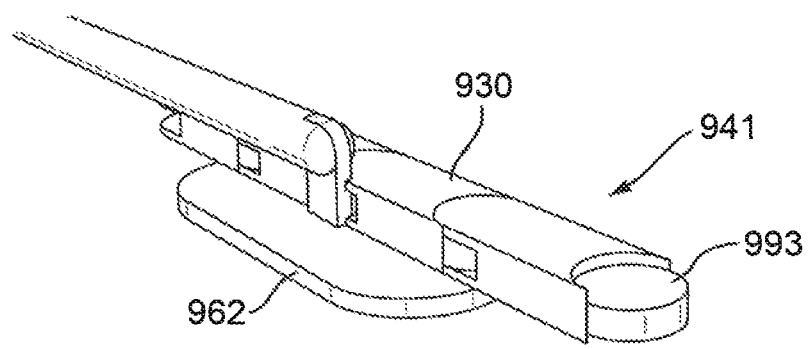
FIG. 13 shows an eighth embodiment of an anvil.
Figure 13B:
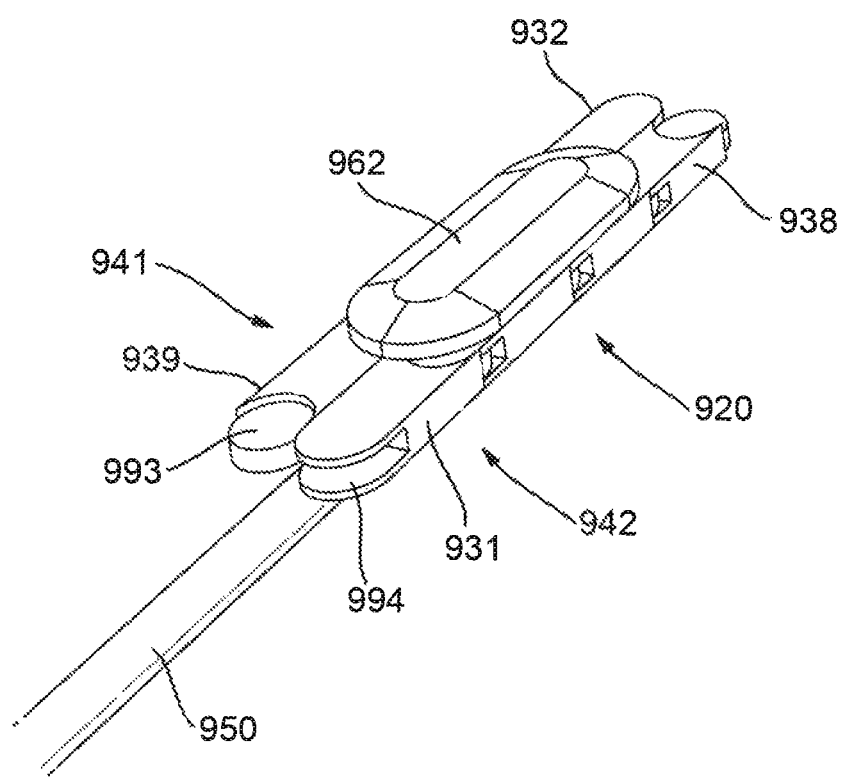
Figure 13C:
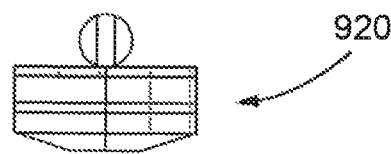
Figure 13D:
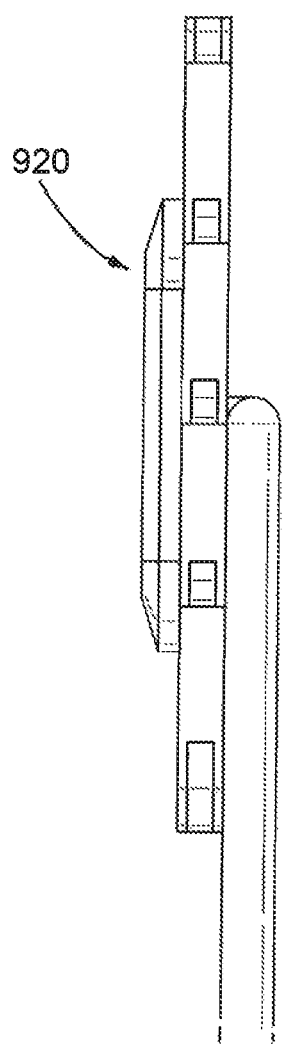
Figure 13E:
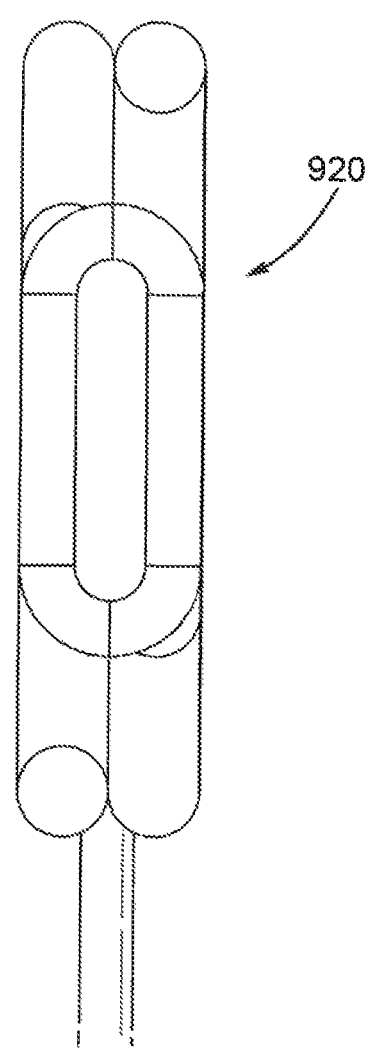

With regard to FIG. 12, this shows a seventh embodiment of an anvil 820. This is similar to the sixth embodiment. However, in the deployed state, the anvil 820 is dome-shape. The dome is substantially continuous.

The dome has a curved periphery and may be a generally solid shape (i.e. there may be no large hole in the centre, unlike the ring). The periphery is circular.

The dome has at its peak the distal end 851 of the shaft 850. This distal end 851 is flared or enlarged, in comparison to the remainder of the shaft 850. The distal end 851 meets with inner surfaces 834 of the segments 830 to form the dome. The segments 830 slope down away from the distal end 851 toward the proximal end with increasing radial distance from the shaft 850.

The segments also comprise cutaways 835 which allow the segments to fit as closely as possible to the shaft in the retracted position.

Unlike the sixth embodiment, in the collapsed state, the anvil 820 is arranged in two lines of segments 830, one line on either side of the shaft 850.

The stapler 101 of the present disclosure comprises a head portion 102 at or toward the distal end of the stapler 101. The shaft 250, 350, 450, 650, 750, 850 and/or the anvil 120, 220, 320, 420, 520, 620, 720, 820 and/or the supporting arm(s) 260, 360, 361, 460, 461, 560, 561, 660, 661, 662, 663, 760, 761, 762 are housed within the head and are extend out from the head in the distal direction, or may be extendable out from the head in the distal direction. This can be seen in FIG. 5.

The head 102 comprises a housing 103 around the shaft 350. The housing 103 takes the form of a tube that has a similar shape (in both size and shape) to the deployed shape of the anvil 320. In FIG. 5, the distal end of the tube 103 is a cylinder.

The distal end of the head 101 may comprises openings 104 for allowing staples to pass through the head 101. The holes 104 are arranged in two concentric rings.

The head 101 and the anvil 320 are arranged and shaped such that when the anvil 320 is in the deployed position, and the stapling operation is carried out, staples are pushed through the holes 104 and through the tissue 114, 115 between the head 101 and the anvil 320. When the staples meet the anvil 320, the anvil 320 provides resistance to the staples so that the staples fold and hold the tissue. This provides a ring of staples.

The ring of staples comprises a double ring of staples.

The head 101 is configured such that the staples can be fired sequentially. The inner ring of staples can be fired first and the outer ring of staples can be fired second (or vice versa).

The head 101 also comprises a sharp edge (not shown) for cutting the tissue between the head 101 and the anvil 320.

Regarding FIG. 13, this shows an eighth embodiment of an anvil 920 that is substantially identical to the second embodiment 320 except where discussed below.

In the deployed position (not shown) the anvil 920 looks substantially similar to anvil 320. However, there are some differences in its collapsed state.

There are eight segments 930 making up the anvil ring.

Instead of the bar 362, the supporting arms are made from a single plate 962. This plate does not sit in between the first collapsed ring half 941 and the second collapsed ring half 942, but instead is offset from the first and second collapsed ring halves 941, 942 in the third direction. The plate 962 is adjacent to and in contact with the segments 930 of the anvil 920.

Further, instead of having all of the segments 330 fixed together by pivots as shown in FIG. 5, in this embodiment the two collapsed ring halves 941, 942 are not permanently attached to one another by hinges 335. All segments 930 of the anvil 920 are attached to adjacent segments by hinges, except for the segments 931, 932, 938, 939 on the ends of the collapsed ring halves 941, 942. These segments instead include an arrangement such that segments 932 and 938 and segments 931 and 939 are held relative to each other when in the deployed state, but are allowed to separate when in the collapsed state. This separation occurs by a mixture of pivoting and sliding motions. Such an arrangement may be one of the segments 938, 939 comprising a tongue 993 and an adjacent segment 931, 932 comprising a groove 994 shaped to accept and cooperate with the tongue 993 when the anvil 920 is deployed.

These differences between the second embodiment and the eighth embodiment allow the segments 930 of the first and second collapsed ring halves 941 and 942 to be adjacent one another (e.g. in actual contact with each other) when in the collapsed state. This reduces the cross-section area of the anvil 920 as can be appreciated from FIG. 13c.

Figure 14:
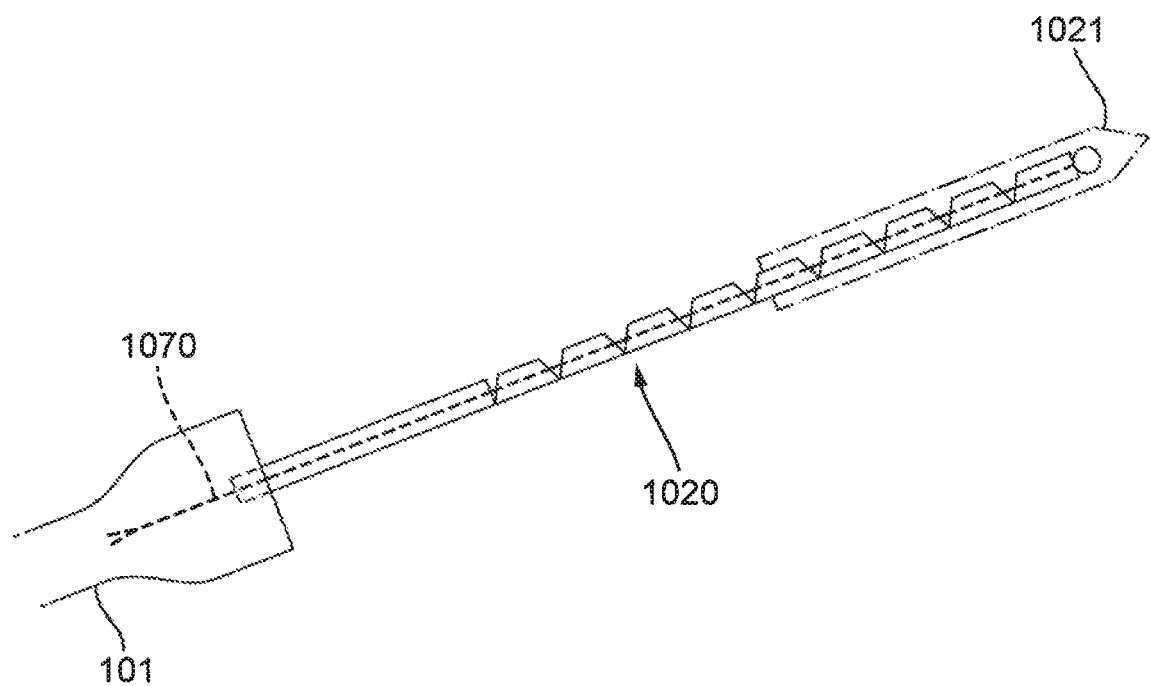
FIG. 14 shows a ninth embodiment of an anvil.

Regarding FIG. 14, this shows a ninth embodiment of the present invention that comprises the stapler 101 and an anvil 1020 that is substantially identical to the anvil 220 of the first embodiment shown in FIG. 4. FIG. 14 shows in more detail the cutting element 121 discussed above in relation to FIG. 2.

Thus, the stapler 101 of FIG. 14 comprises a cutting element 1021. The cutting element 1021 takes the form of a needle-like elongated tube made of plastic that extends in the first direction. The anvil 1020 is located the tube 1021 when the anvil is in the collapsed state. The tube 1021 tapers to a sharp end that is suitable for cutting tissues.

In use, as mentioned above, the stapler 101 is used to staple the closed end of the proximal tube 114 to the closed end of the distal tube 115. The cutting element 1021 cuts through the closed end of the proximal tube 114 only. This occurs when the cutting element 1021 is moved together with the collapsed anvil 1020 toward the distal direction. When the cutting element 1021 and anvil 1020 reach the tissue, the cutting element 1021 cuts through the closed end of the proximal tube 114. Continued movement in the distal direction allows the cutting element 1021 and the anvil 1020, in its collapsed configuration, to pass through the cut hole in the proximal piece of tissue 114 (see FIGS. 2a and 2b). The cutting element 1021 is then removed, as discussed above (e.g. either manually or dissolved). The collapsed anvil 1021 is then inserted through a hole 116 in the closed end of the distal tube 116, which has been created by a cutting means not part of the stapler 101. Once inserted through this hole 116, the anvil 1020 can be deployed and the stapling operation can be carried out (see FIGS. 2c to 2f).

FIG. 14 also explicitly shows the actuating line 1070 that when tensioned actuates the anvil 1020 into its deployed state.

Regarding FIG. 15, this shows a tenth embodiment of the present invention. FIG. 15 shows an anvil assembly 1119 that comprises an anvil 1120 and a first shaft 1150 and a second shaft 1152. Except where discussed below, the anvil 1120 is similar to the anvil discussed in FIG. 5. The anvil assembly 1119 is attachable to and detachable from the remainder of the stapler.

The second shaft 1152 is moveable relative to the first shaft 1150. This movement actuates the anvil 1120. This motion is a combination of a sliding motion along the first shaft 1150, a rotation about the first shaft 1150, and a pivoting away or toward the first shaft 1150.

The first shaft 1150 is attached first support arm 1151, which in turn is pivotally attached to segments of the anvil 1120.

The second shaft 1152 is attached to a second support arm 1153, which in turn is pivotally attached to segments of the anvil 1120.

The second shaft 1152 is connected to the first shaft 1150. This connection is made via a bracket 1180. The bracket 1180 allows the second shaft 1152 to slide (in the first direction) relative to the first shaft 1150, the second shaft 1152 to rotate about the first shaft 1150 when it slides, and the second shaft 1152 to pivot relative to the first shaft 1150 when it slides and rotates. These relative movements are achieved by the use of the bracket 1180. The bracket 1180 comprises a groove 1181 and the first shaft 1150 comprises a peg 1182 that slides in the groove 1181. The second shaft 1152 is housed in the bracket 1180 such that the pivoting movement mentioned above is allowed.

As can be seen in FIG. 15a, when in the collapsed state, the first and second shafts 1150, 1152 are parallel with one another and may be close to one another (preferably touching). As can be seen in FIG. 15b, to actuate the anvil 1120, the second shaft 1152 is moved relative to the first shaft 1150 such that it 1152 slides relative to the first shaft 1150 preferably in a direction toward the proximal end. Due to the groove 1181 and peg 1182 arrangement in the bracket 1180, this sliding motion also causes the second shaft 1152 to rotate relative to the first shaft 1150. Due to these two motions, the second shaft 1152 moves away from the first shaft 1150, and pivots relative to the first shaft 1150 such that the second shaft 1152 is no longer totally parallel with the first shaft 1150.

Due to the relative motion of the two shafts 1150, 1152, the first and second arms 1151, 1153 rotate relative to the two shafts 1150, 1152 and pivot relative to the segments of the anvil 1120. This causes the anvil 1120 to be actuated.

As can be seen in FIG. 15c, the completion of the relative movement of the two shafts 1150, 1152 leads to the anvil 1120 being fully deployed.

Figure 16:
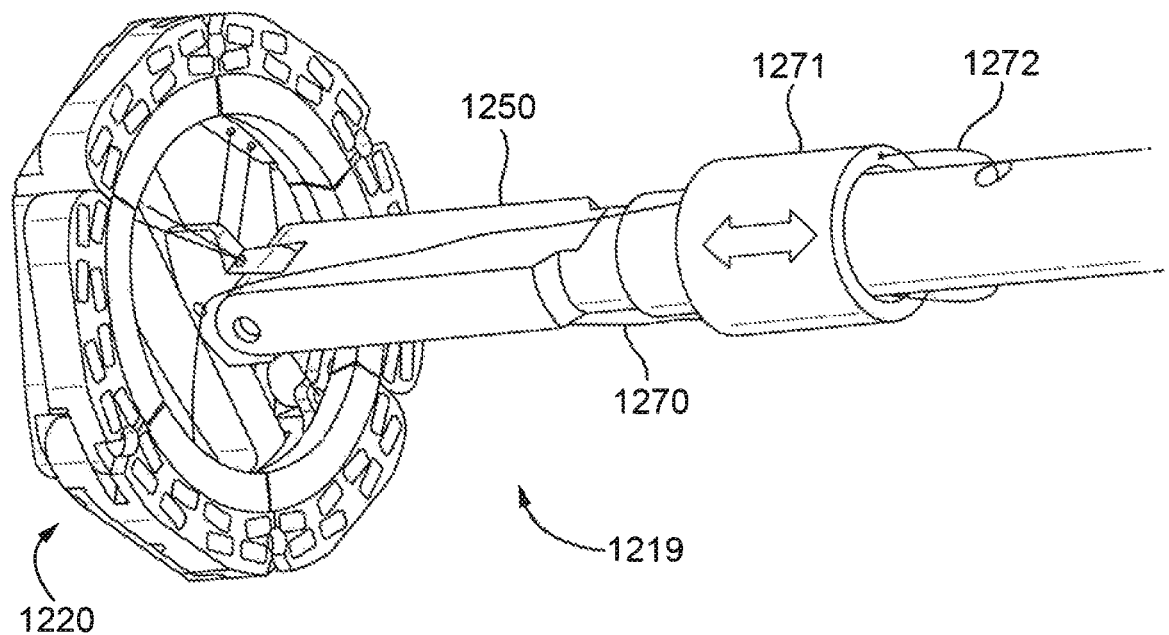
FIG. 16 shows an eleventh embodiment of an anvil as part of an anvil assembly.

Regarding FIG. 16, this shows an eleventh embodiment of the present invention. FIG. 16 shows an anvil assembly 1219 that comprises an anvil 1220 and a shaft 1250. Except where discussed below, the anvil 1220 is substantially identical to the anvil of FIG. 5 and FIG. 7.

Similarly to the FIG. 15 embodiment, the anvil assembly 1219 is attachable to and detachable from the remainder of the stapler. However, in contrast to the FIG. 15 embodiment, a different actuation mechanism is shown. Similarly to FIG. 7, a tension-based actuation system is used. This comprises a plurality of actuator lines 1270. The anvil assembly 1219 also comprises a handle 1271 that connects to the actuator lines 1270. The handle 1271 is placed over or around the shaft 1250 of the anvil assembly 1219. The handle 1271 is attached to the proximal end of the stapler through additional lines 1272. Tension may be applied to lines 1272 by the user, which in turn may apply tension to the lines 1270 via the handle 1271. Tension in the lines 1270 may force the anvil 1220 to actuate as discussed above.

Regarding FIG. 17, this shows a twelfth embodiment of the present invention. FIG. 17 shows an anvil 1320 that is substantially identical to the anvil of FIG. 5 except where discussed below.

Figure 17A:
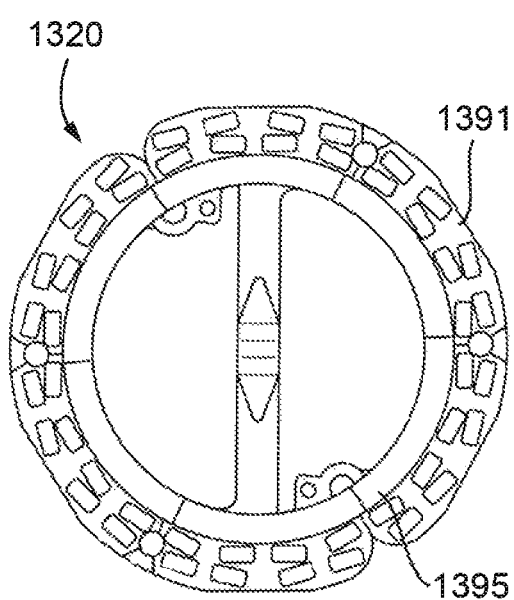
FIG. 17 shows a twelfth embodiment of an anvil.
Figure 17B:
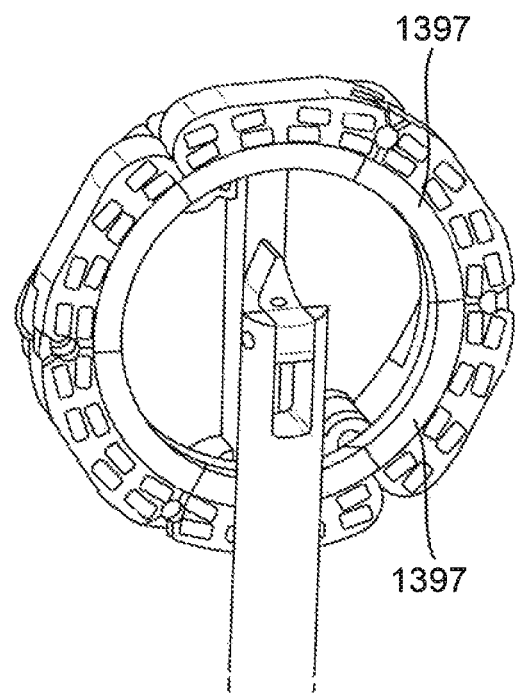
Figure 17C:
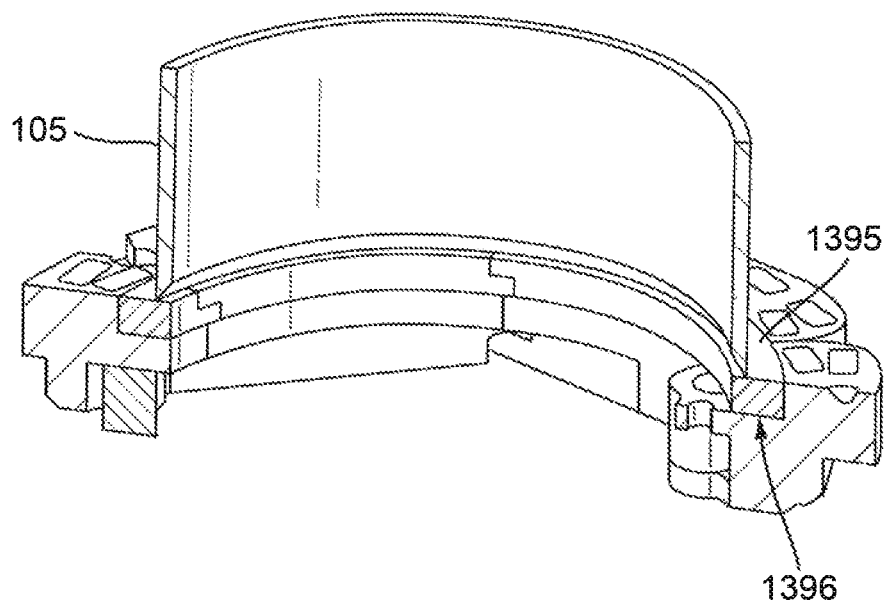
Figure 17D:
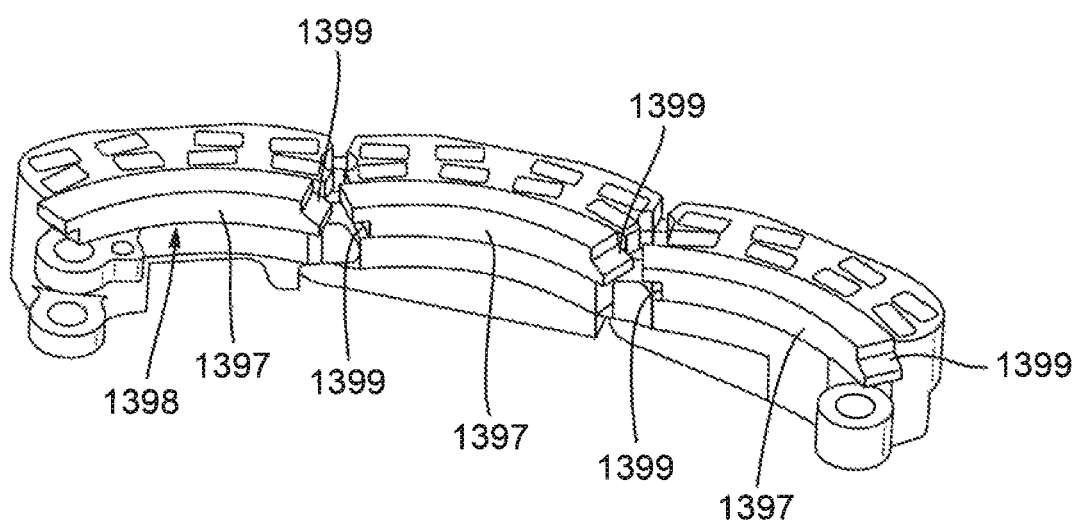

As shown in FIGS. 17a, 17b and 17c, when deployed, the anvil 1320 comprises a cutting surface 1395 that faces toward the proximal end. The cutting surface 1395 is a surface that contacts the tissue and provides resistance to a sharp edge 105 (which may be part of the stapler 101) that cuts through the tissue during the stapling operation. The cutting surface 1395 is made from a resilient material, such as rubber or plastic. The resilient material aids the cutting process.

The cutting surface 1395 is in the shape of an annulus. The cutting surface 1395 is radially inward of the stapling surface 1391.

The shape of the cutting surface 1395 (e.g. the radius and thickness of the annulus) is such that the sharp edge 105 (which is preferably circular and may have a flat circular cutting edge) contacts only the cutting surface 1395 during the cutting operation. This is shown in FIG. 17c.

Also as shown in FIG. 17c, the anvil 1320 comprises a recess 1396 in which the material that forms the cutting surface 1395 is housed.

The cutting surface 1395 is formed of segments 1397. There is one segment 1397 of the cutting surface 1395 for each respective segment of the anvil 1320. The segments of the anvil each comprise a recess 1398 in which respective segments 1397 of the cutting surface 1395 are housed. These recesses 1398 are toward the radially inner portion of the anvil segments.

The segments 1397 of the cutting surface 1395 are fixed to the respective anvil segments. The segments 1397 of the cutting surface 1395 are hence configured to rotate and pivot with the respective anvil segments when the anvil 1320 is deployed or retracted.

The segments 1397 of the cutting surface therefore pivot relative to one another just as the respective segments of the anvil 1320 pivot relative to one another. To allow for this pivoting, the ends of the segments of the cutting surface comprise cutaway portions 1399 that allow for the pivoting whilst forming a complete cutting surface 1395 when the anvil 1320 is deployed.

Whilst certain embodiments have been disclosed above, the skilled person would recognise that it would be possible to combine or select or isolate some of their features for use in other embodiments, as is clear from the above summary of invention section and the appended claims.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. An anvil assembly comprising:
   an anvil for providing resistance to staples during the stapling operation of a surgical stapler, the surgical stapler comprising a proximal end and a distal end wherein the proximal end is proximate to the user in use and the distal end is distal from the user in use:
   wherein the anvil is locatable at the distal end of the surgical stapler, wherein the anvil is configured to be actuated between a deployed state and a collapsed state,
wherein the anvil comprises a plurality of segments arranged end-to-end,
wherein the anvil is elongated in the collapsed state, the anvil being elongated generally in a first direction,
wherein an area covered by the anvil is greater in the deployed state than the collapsed state when viewed along the first direction,
wherein the anvil is configured such that the segments rotate about a rotation axis along a second direction perpendicular to the first direction when the anvil is actuated between the deployed and the collapsed states, and
wherein the anvil is configured such that adjacent segments pivot relative to each other about a pivot axis along a third direction perpendicular to the second direction when the anvil is actuated between the deployed and collapsed states,
a shaft to which the anvil is attached,
wherein the shaft extends in the first direction, wherein the anvil is attached to the shaft by one or more supporting arms, and wherein when in the deployed state the supporting arm(s) is/are orientated substantially perpendicular to the first direction.

2. An anvil assembly as claimed in claim 1, wherein the anvil has a direction of curvature when in the deployed state, and the anvil is configured such that during actuation from the deployed to the collapsed state at least two adjacent segments pivot relative to each other in an inward or outward direction relative to the direction of curvature.

3. An anvil assembly as claimed in claim 1, wherein the anvil is configured such that during actuation from the deployed to the collapsed state all adjacent segments pivot relative to each other in an outward direction relative to the direction of curvature.

4. An anvil assembly as claimed in claim 1, wherein the segments have a length direction and the length direction is orientated substantially parallel or substantially perpendicular to the first direction in the collapsed state.

5. An anvil assembly as claimed in claim 1, wherein in the deployed state the anvil is a ring-shape, a disc-shape or a dome-shape.

6. An anvil assembly as claimed in claim 1, wherein when in the deployed state the anvil comprises a stapling surface that faces toward the proximal end, wherein the stapling surface is a surface that contacts the tissue and provides resistance to the staples piercing through the tissue during the stapling operation, wherein the stapling surface comprises a plurality of recesses shaped and positioned on the surface so as to assist with the folding of the staples piercing through the tissue.

7. An anvil assembly as claimed in claim 1, wherein when in the deployed state the anvil comprises a cutting surface that faces toward the proximal end, wherein the cutting surface is a surface that contacts the tissue and provides resistance to a cutting member that cuts through the tissue during the stapling operation, wherein the cutting surface comprises a resilient material.

8. An anvil assembly as claimed in claim 1, wherein the anvil comprises a peripheral protective portion arranged to protect tissue local to the anvil from being caught in the anvil.

9. An anvil assembly as claimed in claim 1, wherein in the deployed state the supporting arm(s) is/are located at a distal end of the shaft and wherein in the collapsed state the supporting arm(s) is/are located at the distal end of the shaft.

10. An anvil assembly as claimed in claim 1, wherein at least one of the supporting arm(s) is/are located at a distance from the distal end of the shaft.

11. An anvil assembly as claimed in claim 1, wherein in the collapsed state substantially all of the anvil overlaps with the shaft in the first direction.

12. An anvil assembly as claimed in claim 1, wherein at least one of the segments comprises a cutaway portion shaped such that said segment(s) can be fit around the shaft when the anvil is in the collapsed state.

13. An anvil assembly as claimed in claim 1, wherein the shaft is a first shaft, and wherein the anvil assembly further comprises:
a second shaft to which the anvil is attached,
wherein the second shaft extends generally in the first direction, and wherein the anvil is attached to the second shaft by one or more supporting arms.

14. A surgical stapler comprising:
a proximal end and a distal end,
wherein the proximal end is proximate to the user in use and the distal end is distal from the user in use;
an anvil assembly as claimed in claim 1 at the distal end; and
an actuator mechanism configured to actuate the anvil between the deployed and collapsed states,
wherein the actuator mechanism is configured to be controlled from a location on the surgical stapler towards the proximal end.

15. A surgical stapler as claimed in claim 14, wherein the stapler comprises a shaft extending in the first direction, and
wherein the anvil is attached to the shaft by one or more supporting arms; or
wherein the shaft of the anvil assembly is attached to the shaft of the stapler.

16. A surgical stapler as claimed in claim 14, wherein the actuator mechanism comprises a tensioning system configured to apply tension to the anvil.

17. A surgical stapler as claimed in claim 14, further comprising a head portion, the head portion being configured such that staples can be fired from it toward the deployed anvil sequentially.

18. A surgical stapler as claimed in claim 14, further comprising a head portion, the head portion comprising a sharp edge for cutting the tissue, and wherein the sharp edge is sloped with respect to the first direction, or wherein the sharp edge is not sloped.

19. A surgical stapler as claimed in claim 14, wherein the stapler comprises a head portion, wherein the stapler is configured such that when the stapler is actuated the following occur sequentially: the anvil is deployed; the anvil and the head portion are drawn together; and when the anvil is proximate to the head portion the staples are fired sequentially.

20. A method comprising actuating the anvil assembly of claim 1.

21. A method of stapling body tissue using an anvil assembly as claimed in claim 1 and a stapler head, wherein when the anvil is positioned on one side of a piece of tissue to be stapled and the stapler head is on the other side of the piece of tissue to be stapled the following steps are performed sequentially:
drawing the anvil and the stapler head toward together; and
when the anvil is proximate to the stapler head, firing staples from the stapler head through the tissue such that the anvil offers resistance to fold the staples.

* * * * *